(12) United States Patent
Jasanoff et al.

(10) Patent No.: US 11,490,814 B2
(45) Date of Patent: Nov. 8, 2022

(54) TUNABLE DETECTORS

(71) Applicant: Massachusetts Institute of Technology, Cambridge, MA (US)

(72) Inventors: Alan Pradip Jasanoff, Belmont, MA (US); Virginia Spanoudaki, Cambridge, MA (US); Aviad Hai, Madison, WI (US)

(73) Assignee: Massachusetts Institute of Technology, Cambridge, MA (US)

( * ) Notice: Subject to any disclaimer, the term of this patent is extended or adjusted under 35 U.S.C. 154(b) by 344 days.

(21) Appl. No.: 16/536,398

(22) Filed: Aug. 9, 2019

(65) Prior Publication Data

US 2020/0046224 A1 Feb. 13, 2020

Related U.S. Application Data

(60) Provisional application No. 62/716,829, filed on Aug. 9, 2018.

(51) Int. Cl.
*A61B 5/1473* (2006.01)
*A61B 5/055* (2006.01)
(Continued)

(52) U.S. Cl.
CPC .......... *A61B 5/0031* (2013.01); *A61B 5/0084* (2013.01); *A61B 5/05* (2013.01);
(Continued)

(58) Field of Classification Search
None
See application file for complete search history.

(56) References Cited

U.S. PATENT DOCUMENTS

| 6,957,098 B1 * | 10/2005 | Hyde | A61B 5/055 600/424 |
|---|---|---|---|
| 2011/0087080 A1 * | 4/2011 | Schroter | A61B 5/002 600/301 |

(Continued)

FOREIGN PATENT DOCUMENTS

WO    WO 00/38570    * 7/2000    ............... A61B 5/00

OTHER PUBLICATIONS

Control Tutorials for MATLAB & Simulink, dated as early as Jun. 19, 2015 (as evidenced by the cover page showing date by Wayback Machine), pp. 1-16; https://ctms.engin.umich.edu/CTMS/index.php?aux=Activities_LRCcircuitA (Year: 2015).*

*Primary Examiner* — James M Kish
(74) *Attorney, Agent, or Firm* — Wolf, Greenfield & Sacks, P.C.

(57) ABSTRACT

Embodiments described herein relate to detectors and their method of use for sensing electromagnetic fields, electromagnetic signals, biochemical analytes, and/or other conditions in subjects. The device may include an inductively-coupled implantable coil-based transducer that converts electrical, photonic, biochemical signals, and/or other appropriate signals and/or conditions originating in tissues and/or transplanted tissue grafts into changes in a property of the transducer, such as a resonance frequency, that may be detected using an alternating magnetic field that may be provided by a magnetic resonance imaging (MRI) signal and/or other appropriate source. In some embodiments, the detector comprises a FET that changes state upon detection of a subject condition of interest. The change in the FET may change the resonance frequency of an associated LC or RLC circuit. The change in resonance frequency may change the brightness and/or intensity of the detector when detected by an MRI scanner or other appropriate scanner.

20 Claims, 25 Drawing Sheets

(51) Int. Cl.
| | |
|---|---|
| *A61B 5/00* | (2006.01) |
| *G01R 33/48* | (2006.01) |
| *G01R 33/34* | (2006.01) |
| *G01R 33/36* | (2006.01) |
| *G01N 27/414* | (2006.01) |
| *A61B 5/05* | (2021.01) |
| *H01L 31/113* | (2006.01) |
| *H01Q 1/22* | (2006.01) |

(52) U.S. Cl.
CPC ............ *A61B 5/055* (2013.01); *A61B 5/1473* (2013.01); *G01N 27/414* (2013.01); *G01R 33/34084* (2013.01); *G01R 33/3628* (2013.01); *G01R 33/48* (2013.01); *H01L 31/1136* (2013.01); *H01Q 1/2283* (2013.01); *A61B 2562/028* (2013.01)

(56) References Cited

U.S. PATENT DOCUMENTS

| | | | |
|---|---|---|---|
| 2012/0143027 A1* | 6/2012 | Phillips | G01N 27/4145 600/345 |
| 2017/0127975 A1* | 5/2017 | Bozkurt | A01K 11/006 |
| 2018/0131230 A1* | 5/2018 | Mueller | A61N 1/36125 |

* cited by examiner

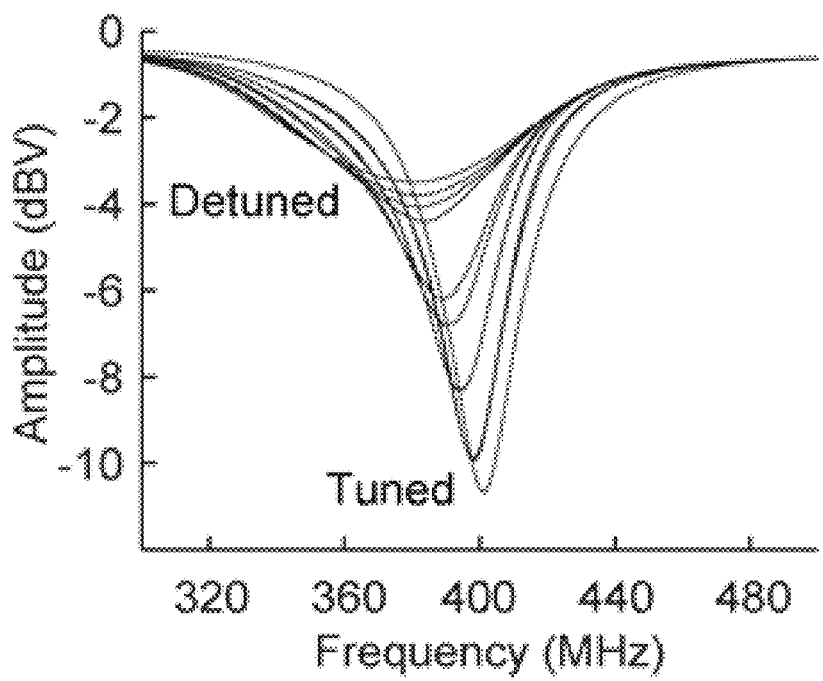
Fig. 5C
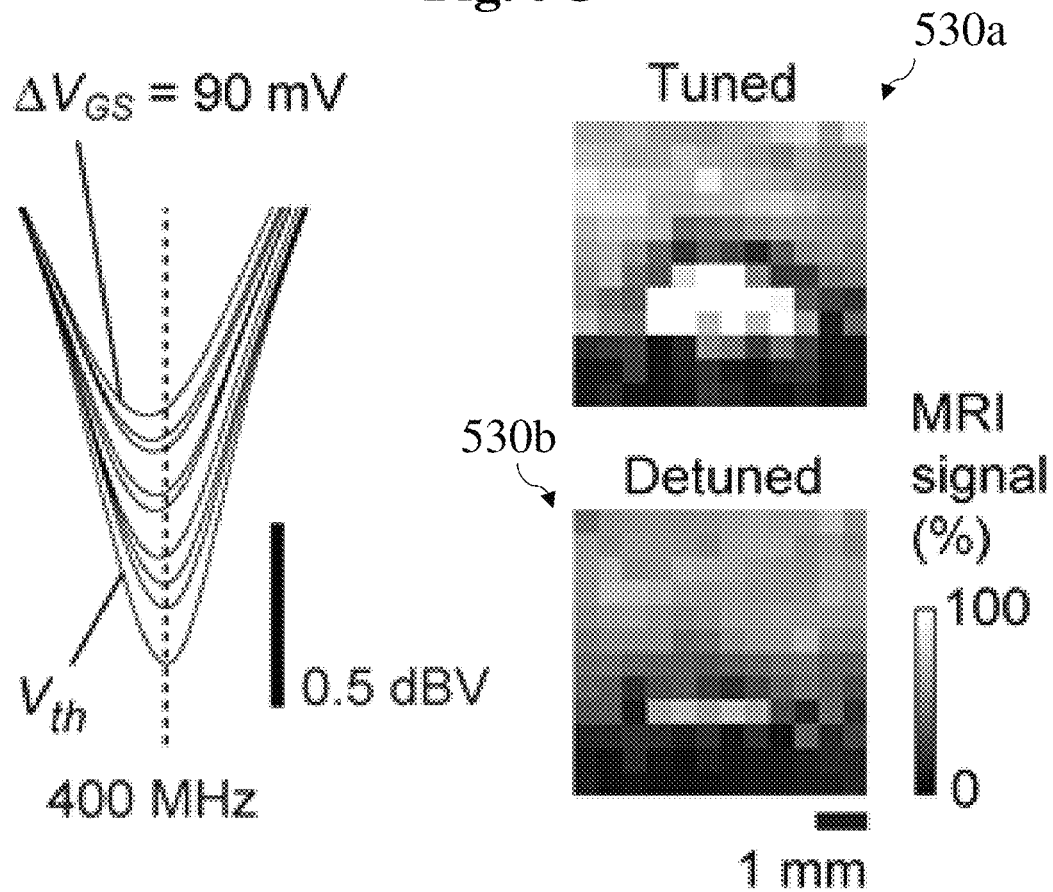
Fig. 5D
Fig. 5E

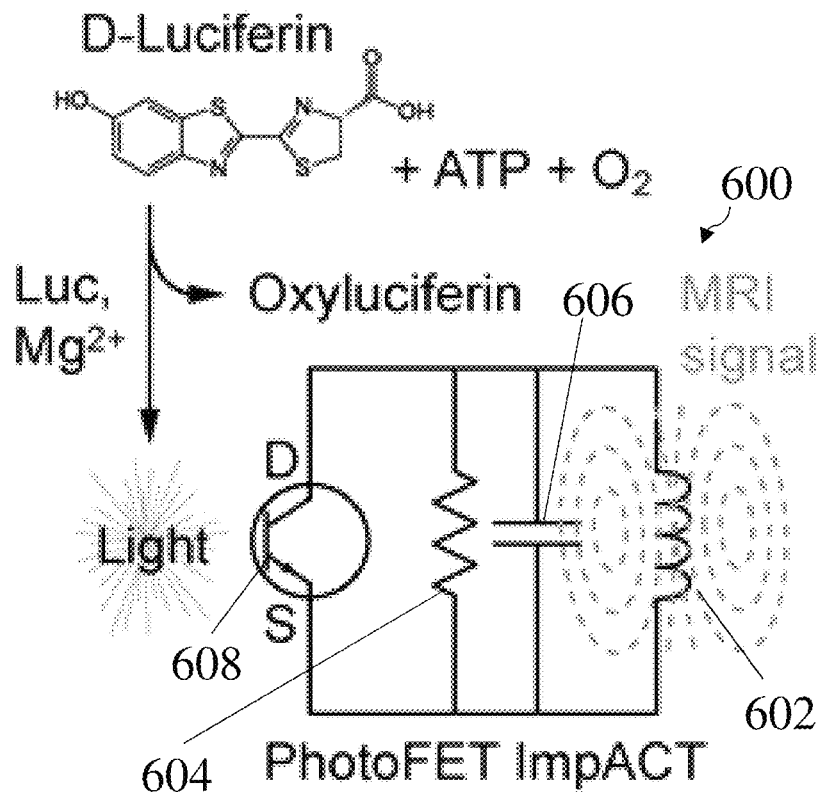
Fig. 6A
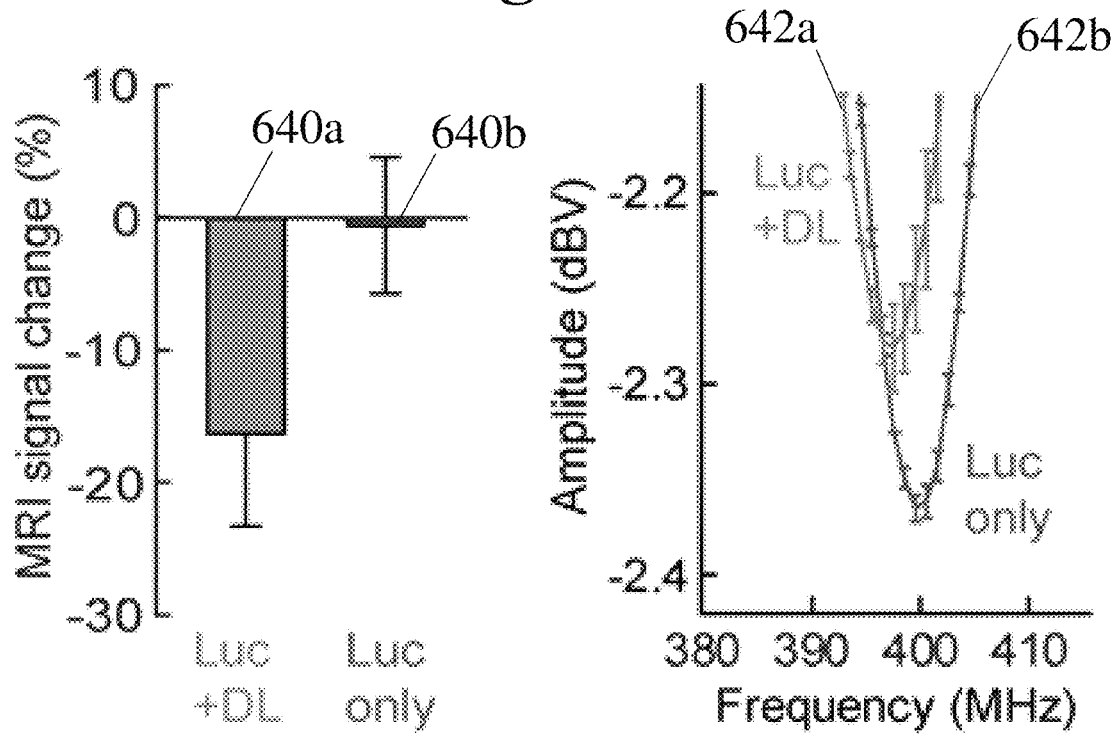
Fig. 6B  Fig. 6C

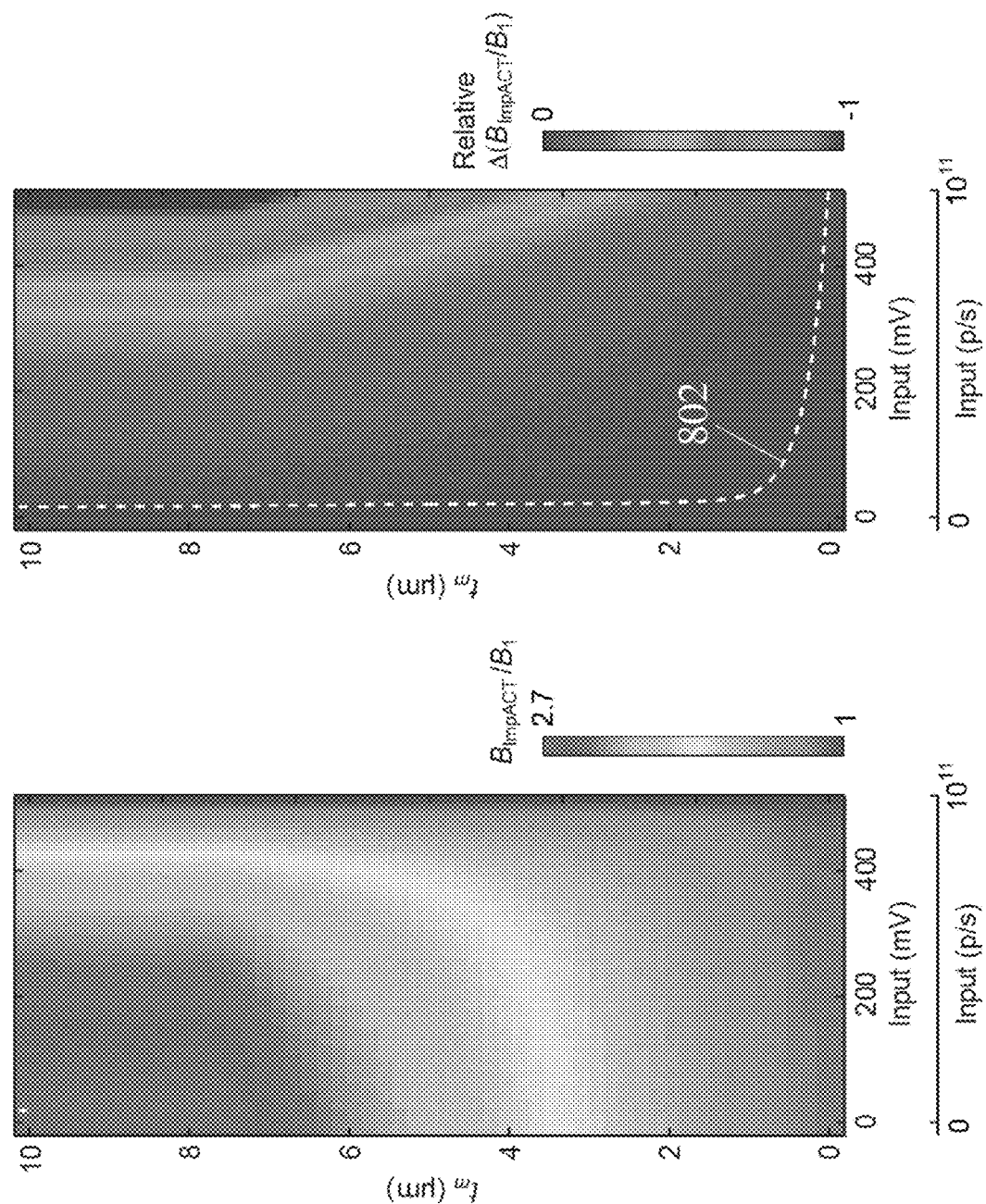

TUNABLE DETECTORS

CROSS-REFERENCE TO RELATED APPLICATIONS

This application claims priority to U.S. Provisional Application No. 62/716,829, filed Aug. 9, 2018, which is incorporated herein by reference in its entirety.

GOVERNMENT LICENSE RIGHTS

This invention was made with Government support under NS076462 and DA038642 awarded by the National Institutes of Health. The Government has certain rights in the invention.

FIELD

Disclosed embodiments are related to implantable tunable medical detectors.

BACKGROUND

Biogenic electromagnetic fields underlie many of the body's most important processes, and form the basis of crucial biomedical technologies for monitoring and diagnosis. In nervous and muscular tissue, electrical potentials are essential to rapid intercellular communication and changes in cellular state. Measuring such signals is fundamental for the study of healthy brain and muscle function, and for characterizing threatening dysfunctions such as those that occur in epilepsy or peripheral neuropathies. Many chemical processes can also be converted into electromagnetic signals using electrochemical techniques; in both preclinical research and clinical settings, such strategies are the basis for monitoring tissue variables ranging from pH in tumors to neurochemical disruptions in Parkinson's disease. Although visible photonic signals do not arise endogenously in mammals, detection of such signals in deep tissue is now the basis for numerous laboratory studies of gene expression and biochemical activity using bioluminescent and chemiluminescent reporters in animal models.

Despite the significance of electromagnetic signal sources in biomedicine, tools for measuring electric, magnetic, and photonic events in tissue are currently severely limited. Macroscopic fields arising from gross muscle contraction and synchronized neural activity can be measured using techniques like electromyography, electroencephalography, and magnetoencephalography, but these methods are very poor at localizing signal origins and cannot discern events at cellular or near-cellular scale. Probes based on glass micropipettes and metal electrodes can be used to record electrical events at a single cell level from neurons and cardiomyocytes in freely moving animals, but require invasive and technically difficult spatial targeting in vivo. Microfabricated arrays of electrodes provide multiplexed recordings of extracellular electrical signals from tens or hundreds of locations in human subjects, but also target relatively few points in space and commonly require invasive, wired connectivity. Although minimally-invasive optical technologies are available for wide-field high resolution neurophysiological recordings through thinned skulls in rodents, these methods are not easily translatable to primates and cannot reliably measure signals below about 1 mm depth. These limitations, coupled with the danger of chronic and acute adverse reactions to both electrical and optical wired probes, highlight the need for new and minimally invasive approaches to the detection of biomedically-relevant electromagnetic fields in opaque tissue.

Probe technologies that interact with noninvasive imaging modalities offer an enticing alternative to more traditional approaches for tetherless detection of electromagnetic fields in biological systems. By converting fields at their sites of origin to changes in localized imaging signals, such probes can avoid the need for powered transmission of information out of the tissue. A recent illustration of this type of strategy employed piezoelectric microcircuits to sense neural activity by converting bioelectric events to ultrasonic waves detectable by a remote transducer. To overcome the attenuation of ultrasound by bone, brain applications may rely on a subdural receiver to amplify the deep tissue signals and convert them to radiofrequency (RF) signals for recording outside the body. Molecular probes suitable for MRI-mediated detection of electromagnetic events have also been introduced; they exploit the superior depth penetration and robustness of MRI-based detection methods. In vitro studies have reported detection of electric field fluctuations using a hydrogel-based MRI contrast agent, as well as photon detection using light-sensitive imaging agents.

SUMMARY

According to one embodiment, a detector includes an antenna as well as an RLC circuit including an inductor, a capacitor, and a resistor. The RLC circuit is electrically coupled to the antenna. The implantable medical detector further comprises a field effect transistor configured to change a resonant frequency of the RLC circuit when a predetermined physical parameter is detected by the field effect transistor.

According to another embodiment, a method includes detecting a predetermined physical parameter with a detector, selectively changing a resonance frequency of the detector between a first resonance frequency and a second resonance frequency when the predetermined physical parameter is detected, and imaging the detector with a magnetic resonance based system.

According to another embodiment, a device includes a circuit configured to electromagnetically couple to an imaging device based on resonant characteristics of the circuit, wherein the circuit is further configured to alter the resonant characteristics in response to detecting a physiological and/or biochemical parameter.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. Some of the below drawings describe figures, graphs, or charts, that are further explained in the detailed description below. In the drawings:

FIG. 5C is a line graph showing network analyzer measurements demonstrating tuning curves for the detector of FIG. 5A over a range of FET gate input values, according to one embodiment;

FIG. 5D is a line graph showing tuning curves of the detector of FIG. 5A in response to millivolt-scale voltage gate inputs, according to one embodiment;

FIG. 5E is an intensity graph showing modulation of an MRI signal by light-gated detuning of the photoFET-based detector of FIG. 5A juxtaposed to a water-based phantom, according to one embodiment;

FIG. 6A is a schematic of bioluminescence detection by a photosensitive detector circuit which may be included in a detector, according to one embodiment;

FIG. 6B is a bar graph showing MRI signal changes measured using the detector circuit of FIG. 6A in the presence of 7.8 μM luciferase with and without addition of D-luciferin (DL), according to one embodiment;

FIG. 6C is a line graph showing measurements of frequency response for the detector circuit of FIG. 6A in the presence and absence of DL, confirming that light production affects MRI signal by detuning the device, according to one embodiment.

FIG. 8A is an intensity graph showing MRI effects modeled as enhancements to the local RF field in the neighborhood of a detector in terms of the detector/MRI field ratio ($B_{ImpACT}/B_1$), as a function of the conductive film thickness ($t_m$) of the detector and the gate input strength in mV or p/s, assuming a detector diameter of d=3 mm, according to one embodiment;

FIG. 8B is an intensity graph illustrating the results of FIG. 8A shown as relative change in local field enhancement in terms of the change of the detector/MRI ratio $\Delta(B_{ImpACT}/B_1)$, according to one embodiment;

DETAILED DESCRIPTION

Figure 1:
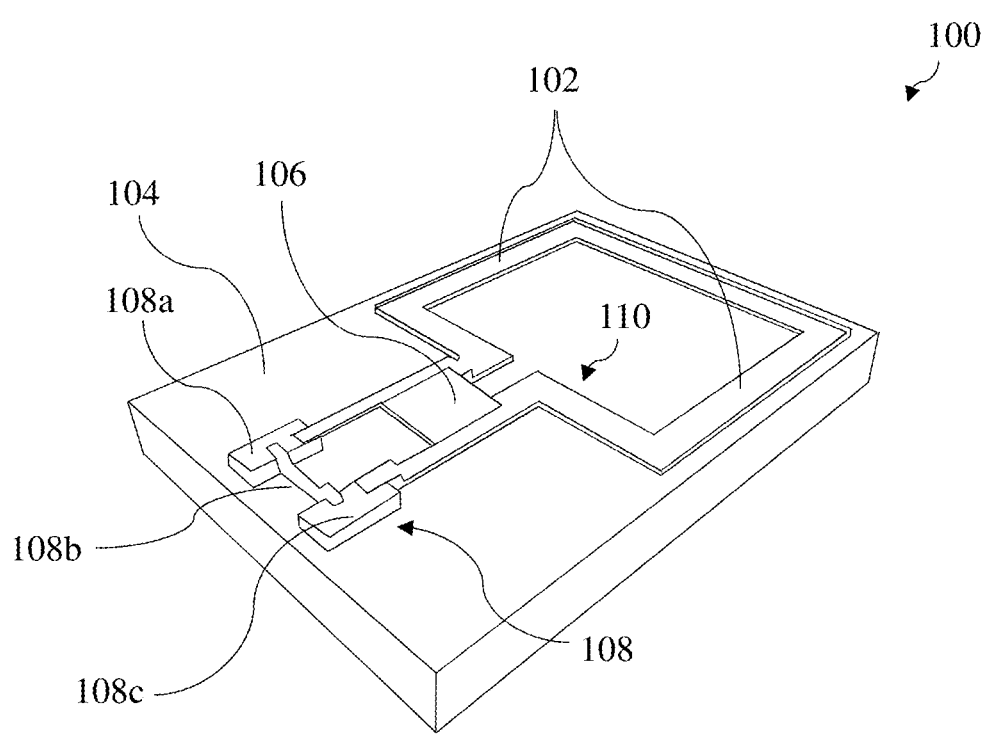
FIG. 1 is a perspective view of an implantable detector, according to one embodiment.

Minimally-invasive measurements of biogenic electromagnetic fields and biochemical analytes are the basis for a wide range of biomedical technologies for the detection, monitoring and study of biophysical and biochemical phenomena. These modalities dominate the market for medical diagnostics and monitoring of healthy and diseased human subjects, as well as biomedical research using animal research models. Macroscopic fields arising from gross muscle contraction, cardiac function and synchronized neural activity can be measured using techniques like electromyography, electroencephalography, and magnetoencephalography, but these methods are very poor at localizing signal origins and cannot discern events at cellular or near-cellular scales. Optical detection of photonic signals in deep tissue using wide-field high-resolution endoscopes is now the basis for numerous laboratory studies of gene expression and biochemical activity using bioluminescent and chemiluminescent reporters in preclinical animal models. These methods, however, are not easily translatable to primates and cannot reliably measure signals below about 1 mm depth. The detection of biochemical analytes can be monitored noninvasively using injectable molecular sensors that are able to target biological processes with high specificity, the dynamic range of detectable signal is limited in the case of PET and MRI, or their signal penetration and consequent three dimensional whole-body or deep-tissue coverage are lacking, in the case of optical methods. Therefore, the inventors have recognized that a minimally-invasive technology for improved measurement and localization of optical, electromagnetic, biochemical, electrochemical, and/other signals of interest near their origin could vastly expand the range of biophysical and biochemical phenomena accessible to monitoring.

Biological electromagnetic fields arise throughout all tissue depths and types, correlating with physiological processes and signaling in diverse organs of the body. Despite the availability of powerful noninvasive imaging modalities, none of these has been sufficiently sensitized to enable detection of biogenic fields in situ, however. This limits monitoring capabilities to spatially restricted recordings using invasive probes, or to poorly resolved surface measurements.

Recognizing the drawbacks associated with the prior detection methods discussed above, the inventors have recognized the benefits associated with an approach for remote sensing of various subject conditions, including, for example, the presence of biochemical analytes, biological electromagnetic fields, optical signals, and other relevant physical parameters. Specifically, the Inventors have recognized the benefits associated with detectors that may be implantable, active, coil-based transducers with states that can be probed noninvasively by using an alternating magnetic field based detection method. These implantable detectors may include resonant circuits that may be inductively coupled to an alternating magnetic field such that a change in a property of the circuit, such as a change in a resonant frequency and/or damping of the circuit in response to detecting a predetermined physical parameter of a subject, may be detected. For example, in some embodiments, a property of a detector may be altered in response to sensing a predetermined physical parameter of a subject such as the presence of electromagnetic fields, biochemical analytes, optical signals, electrochemical signals (for pH, ions, charged entities, or other electrochemical based quantities/concentrations), and/or other relevant physical parameters originating in tissues and/or transplanted tissue grafts. In some embodiments, the alternating magnetic field may be provided by a magnetic resonance imager (MRI) for imaging purposes. For example, MRI typically involves generating a $B_0$ magnetic field in an imaging region and superimposing a varying (e.g., alternating) $B_1$ magnetic field over the $B_0$ magnetic field. In contrast to the varying nature of the $B_1$ field, the $B_0$ field may be roughly constant (e.g., as compared to the dominant oscillating frequency of the varying $B_1$ magnetic field). However, it should be appreciated that any appropriate system capable of detecting a change in the resonance frequency, damping, or other appropriate operating parameter of a detector may be used, as the disclosure is not so limited.

In some embodiments, a detector may comprise an antenna and transistor included in an RLC (resistor, inductor, capacitor) circuit and/or a circuit comprising components with appropriate resistive, inductive, and capacitive properties. In some embodiments, the antenna may be the inductor of the RLC circuit and/or it may provide at least a portion of the inductance in the overall circuit. Additionally, in some embodiments, the antenna may be configured to generate an induced voltage to power the detector in response to an applied varying magnetic field. Without wishing to be bound by theory, the resistance, inductance, and capacitance values of the RLC components can be varied to change one or more resonance frequencies, and/or a damping of the overall circuit. The transistor may act as a sensor that can be responsive to almost any physical parameter of interest depending on the embodiment. When the detector is implanted in a subject, the gate-source voltage of the transistor may be changed upon detection of a physical parameter of interest. In some embodiments, this change in the operating state of the transistor may change the overall circuit's resonance frequency from a first resonance frequency to a second resonance frequency of the circuit. In some embodiments, the first resonance frequency is closer to the resonance frequency of an applied MRI, or other varying magnetic field, signal used to scan the subject. However, embodiments where the second resonance frequency is closer to the varying magnetic field are also contemplated.

Alternatively or additionally, in some embodiments, the change in the operating state of the transistor may change the damping of the circuit at the resonance frequency from a first damping state to a second damping state, as the channel impedance of the transistor may be used to control the amplitude of signals in the circuit at the resonance frequency. For example, the transistor may be controlled from a first impedance state to a second impedance state. The current disclosure may refer to moving from the first resonance frequency to the second resonance frequency which is closer to the scanning frequency as "detuning" and moving from the second resonance frequency to the first resonance frequency as "tuning." Alternatively or additionally, "detuning" may include controlling the transistor from a first impedance state to a second impedance state such that resonant damping increases, and "tuning" may include controlling the transistor from the second impedance state to the first impedance state. When the detector is in a tuned state, the detector may provide a brighter or more intense signal than when in the detuned state due to the detector having a resonance frequency closer to the frequency of the applied varying magnetic field. It should be appreciated that, while a "tuned" detector may exhibit the minimum controllable resonant damping, this is not required, as some damping may be tolerated depending on the desired signal-to-noise ratio of the overall system which incorporates the detector. Likewise, it is not necessary that a "detuned" detector exhibit the maximum controllable resonant damping.

In some embodiments, the disclosed detectors may be fabricated as modified thin film inductor-capacitor circuits. Resonant frequency and/or damping tuning changes may be provided by altering the gate-source voltage ($V_{GS}$) across a transistor, such as a field-effect transistor (FET), placed in parallel, and/or in series depending on the embodiment, with one or more of the other circuit elements. Changes to $V_{GS}$ may close or open the FET, shunting current to or from the coil's inductor and capacitor to alter the resonant frequency of the circuit. Alternatively or additionally, closing or opening the FET may change the channel impedance of the FET to alter the resonant damping of the circuit. In this context, the gate electrode may act as a sensor, and can be configured to be responsive to almost any physical parameter of interest in a similar way that tethered FET-based biosensors function to sense electrophysiological activity, light, and biochemical analytes. In some embodiments, the inductor, such as the antenna, of the circuit may be used to harvest the energy from the applied alternating magnetic field to produce a sufficiently large drain-source voltage ($V_{DS}$) for the device to be in open mode without any bias voltage. It is reasoned that such architectures could therefore provide a versatile basis for rapid detection of a variety of physiological events by MRI and/or the use of any appropriately applied varying electromagnetic field.

The presently disclosed detectors may be used for detecting conditions associated with any appropriate biological structure, including, but not limited to the brain, muscles, organs, and/or transplanted tissues that generate biological electromagnetic fields, photons, are targeted by probes that either fluoresce and/or emit other detectable signals, and/or exhibit biochemical analytes of interest. Using the disclosed detectors and methods, the detection of these signals may be performed using biosensitive implantable microdevices that may be detected using the application of an alternating magnetic field, which may include producing localized image changes in an MRI image. The present disclosure also presents the application of methods discussed herein as well as strategies for their implementation, for the visualization of electromagnetic fields and their origin, distribution and amplitude; for the visualization of spatial and/or temporal patterns of physiological events; for the detection of physiologically relevant biochemical analytes by chemically functionalized detectors; the detection of biophysical and biochemical phenomena; clinical diagnostics; and/or diagnostic imaging.

In view of the above, the inventors have recognized the benefits associated with implantable coil-based transducers for detecting physical parameters of a subject in deep tissue, without the need for onboard power, in conjunction with MRI-based, and/or other appropriate constant or varying magnetic field based, detection and localization techniques. The disclosed detectors may be millimeter or submillimeter-scale implantable devices. In response to biological electromagnetic stimuli, such as voltage or photonic input, biochemical compounds, and/or other physical parameters of interest, the detector may become actively tuned or detuned to an applied varying magnetic field. Specifically, the detector may alter its resonance characteristics (e.g., frequency, damping, etc.) and therefore its ability to couple inductively to the applied varying magnetic field. The strength of coupling between each detector and an applied varying magnetic field, along with the duration and strength of the applied impulses, may determine a brightness and/or intensity of a detected signal.

A method is described for in-vivo imaging of electromagnetic, photonic, biochemical, and/or other physical parameter based signals of biological origins in tissue and organs (including, but not limited to, the brain, heart, muscles, transplanted tissue, and other appropriate biological structures) that are detected using the disclosed detectors. In some embodiments, the detectors may be designed for completely wireless reporting of these events in deep tissue, without the need for onboard power, and in conjunction with MRI-based, and/or other constant or varying magnetic field based, detection and localization technique. Implantable probe technologies that interact with noninvasive imaging modalities offer an enticing alternative to more traditional approaches for tetherless detection of electromagnetic fields in biological systems. By converting fields at their sites of origin to changes in localized signals, such probes can avoid the use of powered transmission of information out of the tissue.

In the above embodiments, a detector's mechanism of detection may use the change of gate-source voltage of the FET to alter the resonance frequency and/or damping of the overall detector. Due to the inclusion of an antenna which may harvest energy from a varying magnetic field, the gate-source voltage change upon detection of a physical parameter of interest may not use a separate power source to function. In turn, a detector may exhibit the detectable tuned and/or detuned states merely by the application of the applied varying magnetic field itself as may occur during MRI imaging. Without wishing to be bound by theory, the $B_1$ magnetic field from MRI scanning, and/or other appropriate forms of applying a varying magnetic field, may induce a voltage and/or current in the antenna to power the circuit. The circuit's detected signal may then reveal whether or not the circuit's resonance frequency and/or damping is either in a tuned or detuned state which is indicative of the desired physical parameter being present or not.

When used for imaging purposes, changes to $V_{GS}$ close or open the FET of a detector may shunt current to or from the coil's inductor and capacitor to change a resonant frequency of the circuit, and/or may provide corresponding changes in impedance that alter resonant damping of the circuit. When detection of a physical parameter detunes the detector, as described earlier, this results in a dimmer or less intense signal from the detector, allowing one reading the MRI results to determine that the signal of interest was detected at the location of the detector implantation in the patient. Therefore, as one of skill in the art should appreciate, implantation of multiple detectors in one subject in different locations and/or at different implantation depths may allow a researcher, pathologist, or other user to detect signals of interest in multiple locations in three dimensions simultaneously.

Depending on the particular embodiment, the physical parameters detected by the disclosed detectors may be: (i) electrical, including neuronal extracellular field potentials, muscle contraction, cardiac activity, neuromuscular synaptic events and central nervous system oscillations; (ii) optical, including photonic signals generated by luminescent cell lines and tissue grafts, and animal models that make use of luminescent reporters; (iii) the concentration of a biochemical analyte, catalytic activity, or gene expression or secretion; (iv) and/or any other appropriate physical parameter.

Figure 11A:
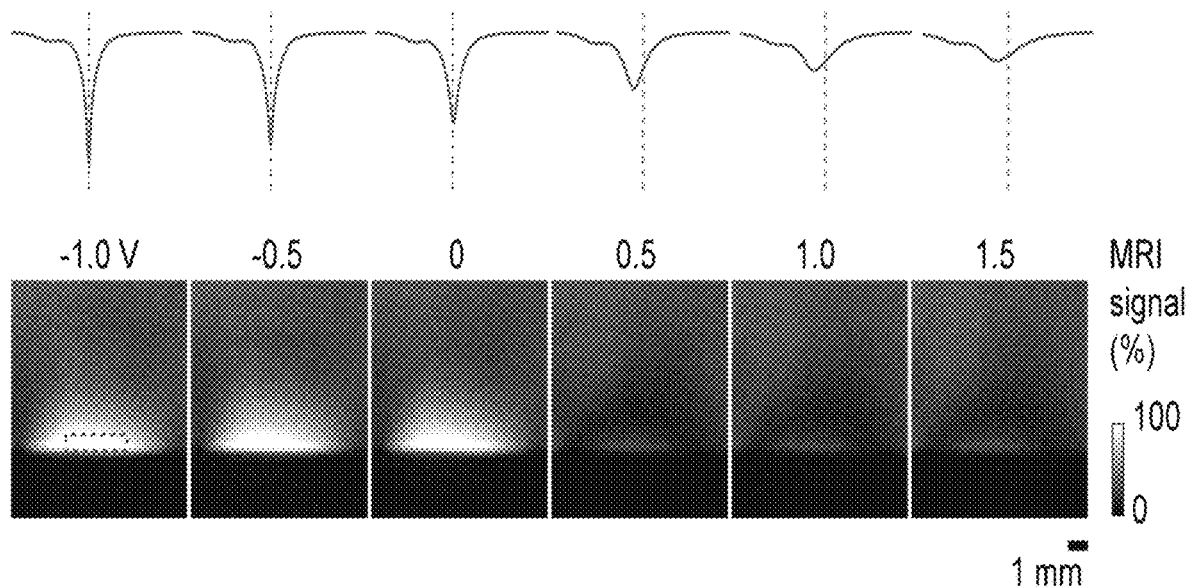
FIG. 11A shows sensitivity of detectors during the application of gate input voltage above $V_{th}$ which detunes the detector and decreases Q, causing a reduction of MRI signal, according to one embodiment.
Figure 11B:
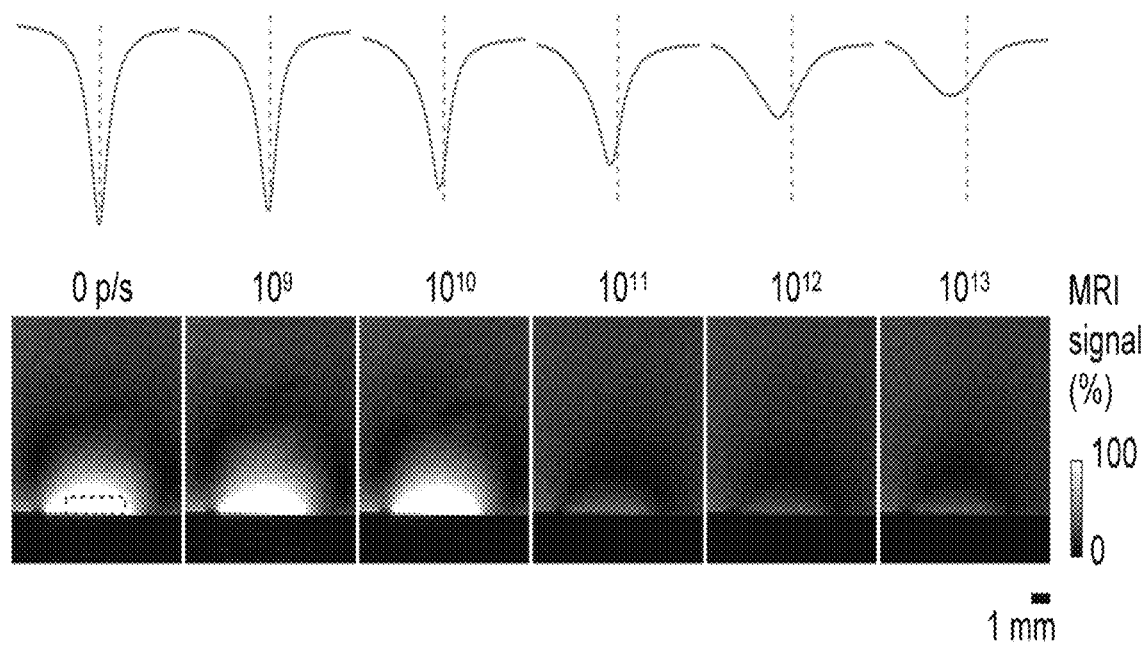
FIG. 11B shows sensitivity during the application of photonic gate input from 0-$10^{13}$ p/s into a photoFET-based detector, according to one embodiment.

Voltage fluctuations of biological origin range from tens or hundreds of microvolts, in the case of neuronal extracellular field potentials, to tens of millivolts in the case of muscle contraction, cardiac activity, neuromuscular synaptic events and oscillations in the central nervous system. To sense these events, a detector according to one embodiment may use an ion-sensitive FET (ISFET). Sensing of voltage by a detector and MRI scanner have been demonstrated (FIG. 1 and FIGS. 11A-11B). The sensing relies on the same principles of commonly used, tethered FET-based biosensors that can sense electrophysiological activity by modulating the FET gate-source voltage ($V_{GS}$) in response to charge fluctuations at or near the sensing gate electrode.

The presently disclosed methods of constructing and using a voltage sensitive detector to sense tissue voltage include fabrication of detector circuit components on different substrate types (for example glass, polyimide) using integrated circuit fabrication processes; delivery of detectors to tissue sites of interest by means of injection or implantation, and use of proper MRI scanning protocols, pulse programs, and MRI RF coil hardware that interact with the detectors for optimal tuning and sensitivity.

Figure 6D:
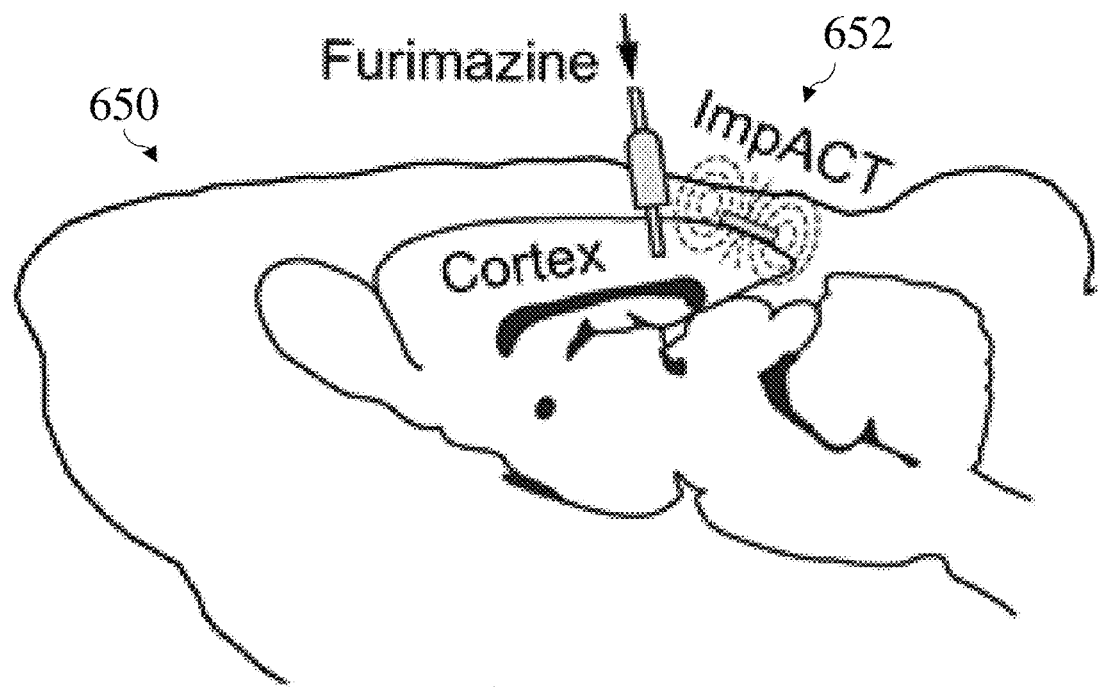
FIG. 6D is a 2D schematic of MRI monitoring of bioluminescent cells in a live rat brain using the detector circuitry of FIG. 6A, according to one embodiment.
Figure 6E:
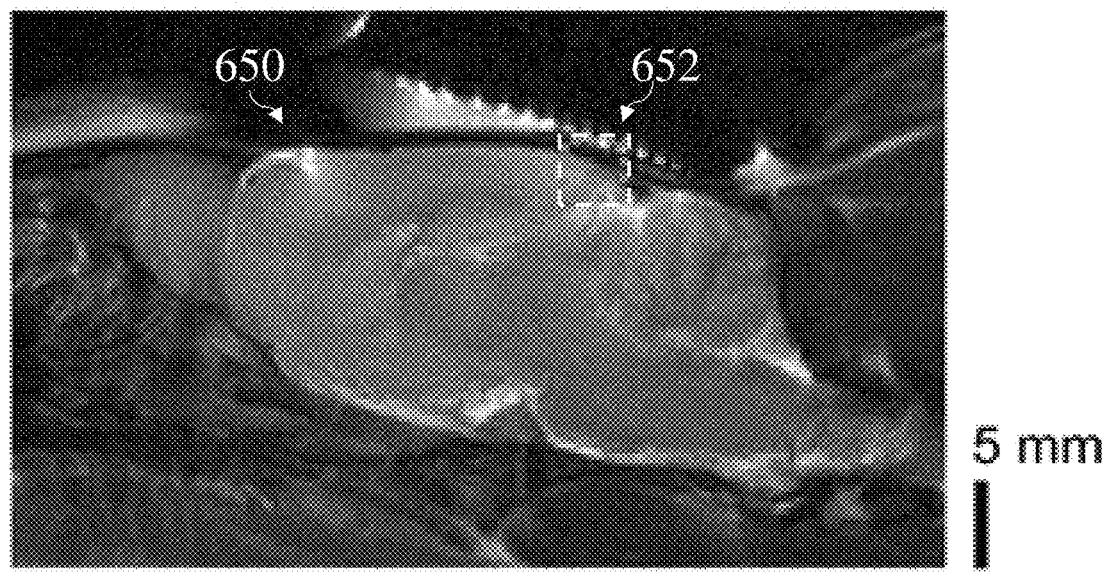
FIG. 6E is an anatomical MRI scan of the rat brain of FIG. 6D showing the region of image signal modulated by the detector, according to one embodiment.
Figure 6F:
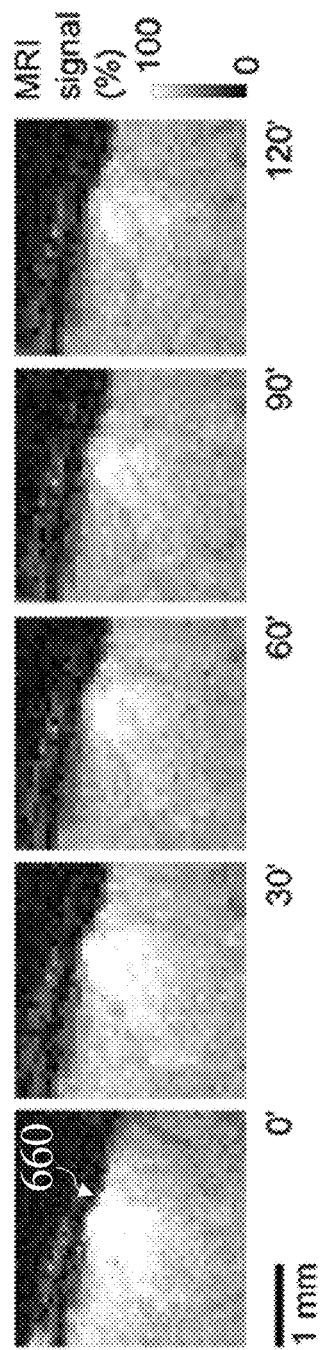
FIG. 6F shows close-up images obtained from imaging the rat brain of FIG. 6D at t=0, 30, 60, 90 and 120 minutes before, during, and after furimazine infusion (t=5-35 mins)

Photonic signals generated by luminescent cell lines and transgenic animal models that express bioluminescent probes can reach flux values of $10^{10}$ photons per second or more, depending on which luminescent reporter was used and on the factors regulating its activity. Cellular expression of luciferase is widely used in vivo as a reporter for cell density and status in animal models of tumorigenesis and transplantation. To sense biogenic or chemogenic photonic events, the detectors according to one embodiment may use a photo-sensitive FET (photoFET) in parallel with the other circuit elements. Sensing of bioluminescent cell lines transplanted in live brains by photo sensitive detectors and detected by MRI scanner have been demonstrated (FIGS. 6D-6F).

Biochemical analytes can be sensed by electrochemical electrodes and field effect transistors that are functionalized by biochemically responsive molecules such as enzymes, antibodies and receptors. Such devices are used in both preclinical research and clinical settings, and are the basis for monitoring tissue variables ranging from pH in tumors to neurochemical disruptions in Parkinson's disease. The chemically sensitive detectors according to one embodiment may be sensitized to sense biochemical analytes, via functionalization of the gate electrode of ion-sensitive FETs with biochemically active agents, allowing for detection of diverse analytes with high specificity, in proportion to their concentration, via enzymatic or biochemical recognition events that alter transconductance of the FET.

Implementations of the aforementioned strategies can further be applied for at least the visualization of cardiac, neural and muscular electrophysiological activity, for the visualization of spatiotemporal patterns of gene expression, and diagnosis and monitoring of biochemical markers related to disease.

Millimeter- and sub-millimeter-scale voltage-sensitive detectors can be deployed in the brain, heart, muscles, and/or other organs of the body where monitoring of electromagnetic fields is desired. Device dimensions could be minimized to allow for placement using endoscopic procedures, or perhaps even infusion into vasculature in both humans and model animals. Photon-sensitive detectors can be used to detect bioluminescent calcium sensitive probes correlated with brain activity in transgenic animals.

Although sufficiently visible photonic signals do not arise endogenously in mammals, detection of such signals in deep tissue is now the basis for numerous laboratory studies of gene expression and biochemical activity using bioluminescent and chemiluminescent reporters in animal models. Photon-sensitive detectors can be placed at the organ or tissue of choice that is expressing luminescent reporters, and is under the control of promoters of interest, to achieve localized readouts specific to expression of a gene of choice.

Chemically sensitive detectors can be functionalized with enzymes, receptors and antibodies to detect and monitor chemical species in healthy or diseased patients. The devices can be implanted subdermally, or at target organ and used for long-term, minimally invasive and safe sensing of biochemical markers related to specific pathologies.

The disclosed methods may be applied for at least scientific investigation of physiological and biochemical phenomena; testing or screening of substances for pharmacological or pharmacokinetic properties; clinical diagnostic imaging. The design features and usage of the disclosed detectors are described further below, including device fabrication process, circuit components, composition and material types, tuning methods of resonant detectors, and their applications to the detection of electrical, photonic or biochemical phenomena.

Wireless radio-frequency (RF) powered devices have been used to monitor neurophysiology, muscle contractions, and biochemical analytes in humans and animal models. However, probe technologies that interact with noninvasive imaging modalities have not been shown, and can offer an enticing alternative to more traditional approaches for tetherless sensing in tissue. Firstly, by converting signals at their sites of origin to changes in localized imaging readout, the disclosed detector technology cancels the need for powered transmission of information out of the tissue. Secondly, the localization of the measured phenomena is straightforward and inherent by means of the inherent three dimensional capabilities of MRI readout.

Visible photonic signals arising from bioluminescent and chemiluminescent reporters, coupled to biochemical and genetic pathways, are currently detected in deep tissue using various minimally-invasive optical technologies. However, many of these methods are not easily translatable to primates and cannot reliably localize signals in three dimensions, and below about 1 mm depth. These limitations, coupled with the danger of chronic and acute adverse reactions to both electrical and optical wired probes, highlight the need for new and minimally invasive approaches to the detection of biomedically-relevant photonic signals in opaque tissue. detector technology offers a minimally-invasive technology for improved measurement of optical signals near their origin, that measured by noninvasive MRI modality, and could thus vastly expand the spatial characteristic of physiological phenomena accessible to monitoring. Miniaturization of the devices to sub-millimeter scale will permit placement using endoscopic procedures or infusion into vasculature.

Contrast agents have been previously developed for molecular fMRI, and are able to sense biochemical phenomena. These contrast agents are synthetic molecules, proteins, or nanoparticles which (1) darken or brighten an MRI image by virtue of their magnetic properties and (2) do so in a manner that is dependent on a biochemical and molecular signal of interest. While the function and utility of these contrast agents has been demonstrated in vitro, in cell culture, and in live animals, they have some limitations that can be concretely circumvented by detectors to modulate the MRI signal. Firstly, no design of fMRI contrast agents has been demonstrated to detect charge fluctuations in tissue. A voltage-sensitive probe as described herein can open the door to using fMRI for a volumetric detection of electric fields in the body in deep tissue and precise localization. Secondly, while some prior work showed detection of photons by contrast agents, their sensitivity and dynamic range are low, and do not reach the inherent detection capabilities of photosensitive transistors as described herein. The technology disclosed herein will allow for long-term monitoring of luminescence, using an implanted detector, that is not cleared out of the tissue.

Of course while particular advantages are described above, certain embodiments of the disclosed detectors may exhibit a subset of the described advantages and/or different advantages as the disclosure is not so limited.

The disclosed detectors may be used in a number of different applications. For example, the disclosed detectors may be used in biomedical research and development as well as clinical diagnostics, and clinical diagnostic imaging. In research and development, both basic biological discovery and drug development will benefit. Primary scientific motivations in the area of neuroscience and physiology, exemplify the application of the described technology to gain functional physiological understanding of the biology of a major disease area, which may lead the discovery of addressable functional mechanisms in health and disease. For drug development, pharmacological screening and characterization will benefit from the advantages of the approach discussed herein. Using volumetric biophysical and biophotonic readouts will enhance the study of drug effects in the same way as the study of natural physiological phenomena. In clinical diagnostics and imaging, implantable MRI probes will allow visualization and three-dimensional localization of electrical and biochemical phenomena. Examples include (i) seizure localization in epileptic patients in the case of electrical activity (ii) tumor markers in different organs in the case of biochemically functionalized detectors. Specific applications may include neuroimaging, clinical diagnostics, and specific disease detection. While use of the disclosed detectors is primarily described relative to medical applications where detectors are positioned in the body for detecting a desired physical parameter, applications where the disclosed detectors are positioned in non-optically accessible locations outside of the body for measuring one or more predetermined parameters including the presence of various chemicals, environmental parameters (e.g. temperature, pressure, etc.), radiation, light, etc. are also contemplated as the disclosure is not so limited.

While the disclosed embodiments are primarily described relative to the use of field effect transistors (FETs), it should be understood that the various disclosed embodiments may be used with any suitable transistor. The use of the name FETs or field effect transistors is merely one example of the various types of transistors that can be used in the described detectors. For example, bipolar junction transistors (BJTs), heterojunction bipolar transistors (HBTs), and other suitable transistors may be used in place of or in addition to FETs. Accordingly, as used herein, "source" may refer to an emitter, "drain" may refer to a collector, and "gate" may refer to a base. Moreover, n-channel and/or p-channel transistors may be used in accordance with various embodiments having different circuit configurations.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 shows an implantable detector 100 according to one embodiment. Structurally, the detector 100 includes a thin-film conductive layer 110 deposited onto and/or within a substrate 104, which may have one or more layers. In the illustrated embodiment, the substrate 104 is a printed circuit board. In further embodiments, the substrate 104 may be a semiconductor substrate such as silicon. As illustrated, a capacitor 106 and an inductor 102 are included (e.g., formed) on the substrate 104. In embodiments in which the substrate 104 is a semiconductor substrate, components formed and/or placed thereon may be disposed in a semiconductor package. The detector 100 further includes an antenna, which is illustrated as the inductor 102. However, embodiments in which an antenna separate from the inductor 102 may be included are also contemplated. The capacitor 106 is electrically coupled to the inductor 102 to form an LC circuit. In some embodiments, one or more resistors (not shown) can be placed throughout the circuit depending on the desired resonance damping properties to form an RLC circuit as well. In other embodiments, a resistance of the conductive layer 110 (e.g., overall or in certain portions) may be controlled to provide damping for the RLC circuit. As detailed further below, a field effect transistor (FET) 108, which may include a source 108a, gate 108b, and drain 108c, may be electrically connected in series and/or parallel with the capacitor 106, antenna, inductor 102, and/or resistor of the circuit. In embodiments in which the substrate 104 is a semiconductor substrate, the FET 108 may be fabricated by doping portions of the substrate 104 to form a channel connecting the source 108a and drain 108c terminals, with the channel controlled by the gate 108b. In some embodiments, the FET 108 may be a metal oxide semiconductor FET (MOSFET), and so an oxide layer may be deposited between the channel and the gate 108b. In embodiments in which the substrate 104 is a printed circuit board, the FET 108 may be formed and packaged individually and placed on a surface of the printed circuit board. In any case, depending on the state of the FET, the resonance frequency and/or damping of the overall circuit may be changed, such as between at least a first resonance frequency and a second different resonance frequency, and/or between a first damping state and a second damping state.

Figure 3A:
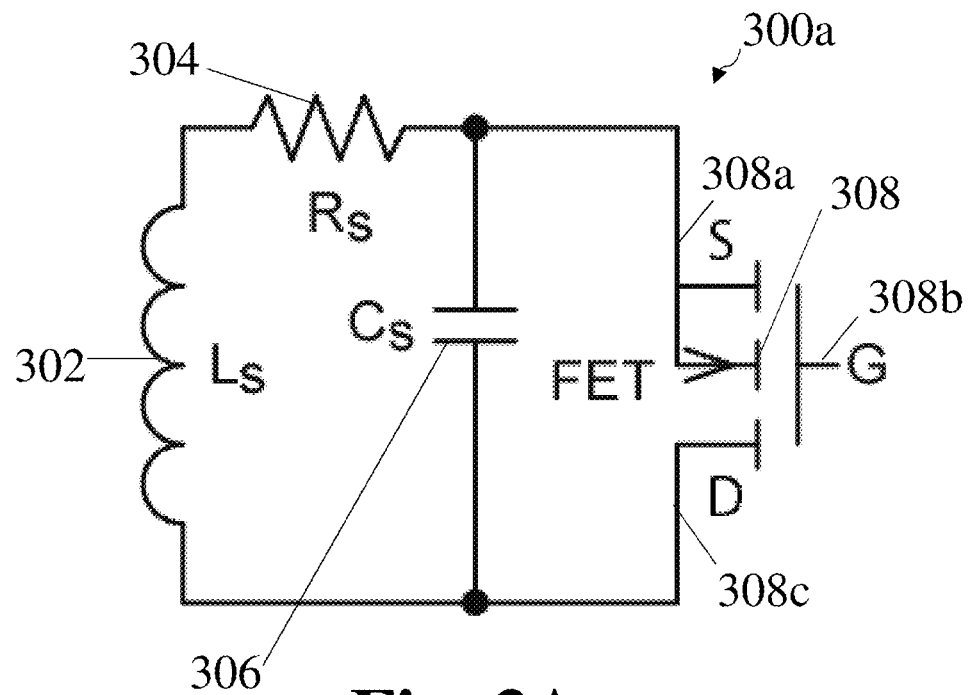
FIG. 3A is a circuit diagram showing circuitry which may be included in a detector, according to one embodiment.
Figure 3B:
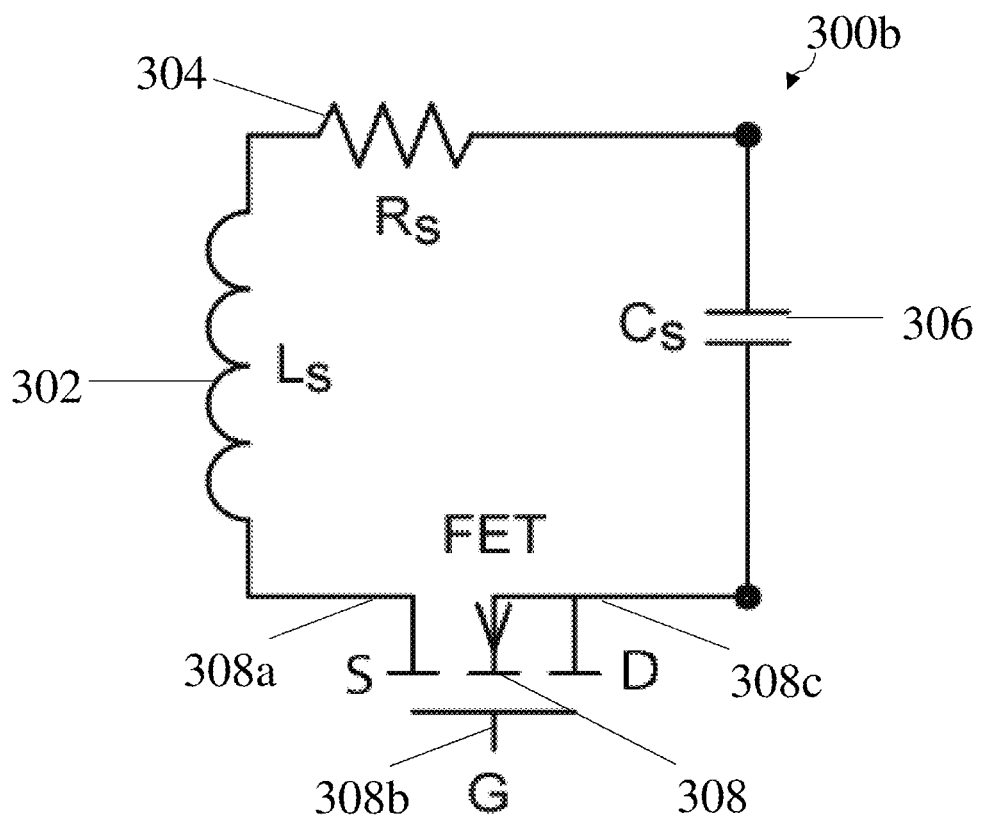
FIG. 3B is a circuit diagram showing alternative circuitry which may be included in a detector, according to one embodiment.

While a particular circuit is described relative to FIG. 1, it should be appreciated that other circuit configurations are possible for the detector 100, as described further herein including with reference to FIGS. 3A-3B.

In the illustrated embodiment of FIG. 1, the FET 108 is positioned in parallel with the capacitor 106, such that depending on a controlled channel impedance of the FET 108, current may be shunted to the channel of the FET away from the capacitor 106. The resonance frequency of an LC circuit generally depends on the time taken for an inductor and a capacitor to charge and discharge one another. Accordingly, the time taken to charge and/or discharge the capacitor 106 and/or inductor 102 may be altered by shunting current away from the capacitor 106. Thus, the resonant frequency of the detector 100 may be controlled based on the channel impedance of the FET 108.

As described further herein, FETs may be controlled by various physiological and/or biochemical phenomena, such that resonant characteristics of detectors may be altered upon detection of such phenomena. For example, depending on the FET 108 used, the sensor can be sensitive to voltage and ions (Ion sensitive FET—ISFET), light (Photo sensitive FET—PHOTOFET), biochemicals in the body (Chemically sensitive FET—CHEMFET), and/or any other appropriate physical parameter of interest of a subject. However, other FET types are considered including but not limited to: Biologically sensitive FET (BioFET), Enzyme Modified FET (EnFET), antibody sensitive and antigen functionalized FET (ImmunoFET), nanowire FET (NWFET), silicon nanowire FET (silicon NWFETs), Bipolar junction transistors (BJTs) in NPN or PNP configuration, Magnetic Field Sensitive metal oxide silicon FET (MAGFET), or combinations of the previous types.

Figure 2A:
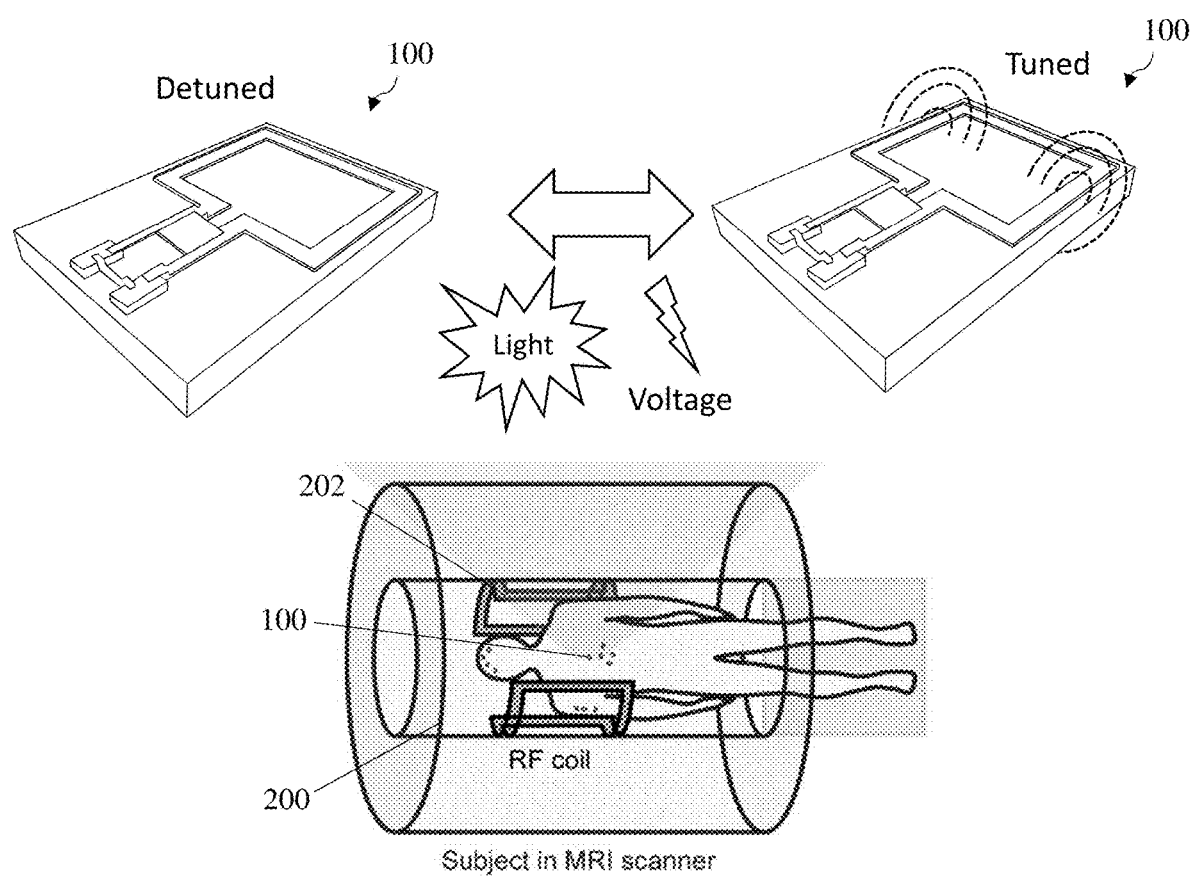
FIG. 2A is a schematic showing the detector of FIG. 1 in use during in vivo imaging, according to one embodiment.
Figure 2B:
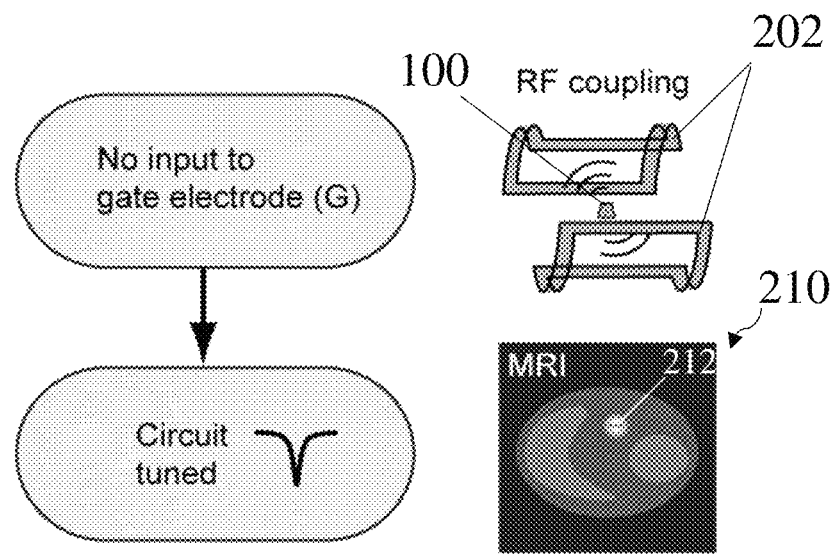
FIG. 2B is a schematic illustrating the behavior of the detector of FIG. 1 within a magnetic field in a tuned state, according to one embodiment.
Figure 2C:
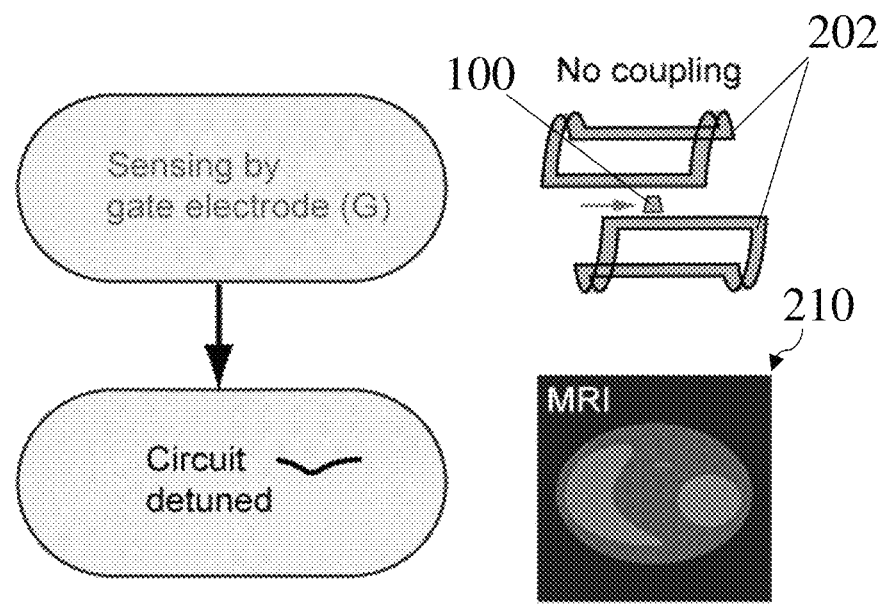
FIG. 2C is a schematic illustrating the behavior of the detector of FIG. 1 within a magnetic field in a detuned state, according to one embodiment.

FIGS. 2A-2C show exemplary operation of a detector 100 during use as an imaging probe for functional MRI (e.g., within an implantable active coil based transducer (IMPACT)). As shown in FIG. 2A, detector 100 may be implanted in a human subject, and the subject may be located within an MRI machine 200. RF coils 202 of the MRI machine 202 produce a varying magnetic field that may resonate with the detector. For example, the varying magnetic field may have a same resonant frequency as a tuned resonant frequency of the detector 100. As represented in FIG. 2A, when the detector 100 is tuned as a result of change in the gate-source voltage of the FET 108 upon detection of a signal of interest, the detector 100 resonates more intensely than in its detuned state. For example, the resonant frequency of the detector may better align with the frequency of the varying magnetic field when the detector 100 is in its tuned state, and/or the detector 100 may have less resonant damping at the frequency of the varying magnetic field, facilitating coupling between the detector 100 and the RF coils 202. Moreover, FIG. 2A illustrates how voltage, such as induced by detection of light (e.g., using a photo-FET) may control the transistor 108 to change impedance states and alter resonance characteristics of the detector 100.

FIGS. 2B-2C show the operation of the detector 100 and the MRI scanner. FIG. 2B shows operation when a physiological and/or biochemical phenomena (or an absence thereof) does not control the FET 108 to alter to the resonant characteristics of the detector 100, thus facilitating the detector 100 to remain in the tuned state. Accordingly, the detector 100 is coupled to the RF coil 202. In the tuned state, inductive coupling between the RF coil 202 and the detector 100 produces local enhancement in MRI scan 210, as illustrated by the illuminated portion 212. Comparatively, FIG. 2C shows operation when such phenomena controls the FET 108 to alter the resonant characteristics of the detector 100, resulting in detuning of the detector 100, and interrupting inductive coupling between the detector 100 and the RF coil 202. Accordingly, the MRI signal enhancement is not present, indicated by the absence of illuminated portion 212.

FIGS. 3A-3B show resonant circuit configurations 300a and 300b which may be included in a detector 100, each having different positioning of the resonating circuit elements (RLC) and the FET 108. FIG. 3A shows an electrical circuit 300a including an inductor 302 and resistor 304 coupled in series. A FET 308 and a capacitor 306 are coupled in parallel with one another, and also in parallel with the series-coupled inductor 302 and resistor 304. The parallel coupling of the FET 308 and the capacitor 306 may facilitate control of the resonant frequency by the operating state of the FET 308, as the channel impedance of the FET determines an amount of current shunted from the capacitor 306 and/or inductor 302, affecting the resonant frequency of the circuit 300a.

FIG. 3B shows an alternative configuration with the inductor 302, resistor 304, FET 308, and capacitor 306 all coupled in series with one another. As illustrated, the channel impedance of the FET 308 adds to the resistance of the resistor 304 to provide resonant damping of the circuit 300b. Thus, when the FET 308 is in a high channel impedance state, the resistance of the circuit 300b is large and provides correspondingly large resonance damping. As an extreme example, when the FET 308 is an open circuit, the corresponding resonant damping is so significant that no resonance at the resonant frequency of the circuit 300b is possible. Further, when the FET 308 is in a low channel impedance state, the damping of the circuit may be almost entirely provided by the resistor 304, with the theoretical minimum possible resistance of the circuit 300b being equal to the resistance of the resistor 304. However, it should be appreciated that the FET 308 need not be completely open or completely closed to provide an effective amount of damping or lack thereof for operation as described herein. Further, it should be appreciated that the FET 308 can be placed in series and/or parallel with any of the resistor 304, inductor 302, and/or capacitor 306 of the circuit 300b to provide the desired change in resonance frequency and/or damping depending on the channel impedance state of the FET 308. Additionally, the depicted diagrams are merely illustrative. In reality, any appropriate number and combination of electrical components including components other than those depicted in the figures may be included in a circuit as long as the circuit includes the FET and retains the ability to change resonant frequencies and/or damping.

Figure 4A:
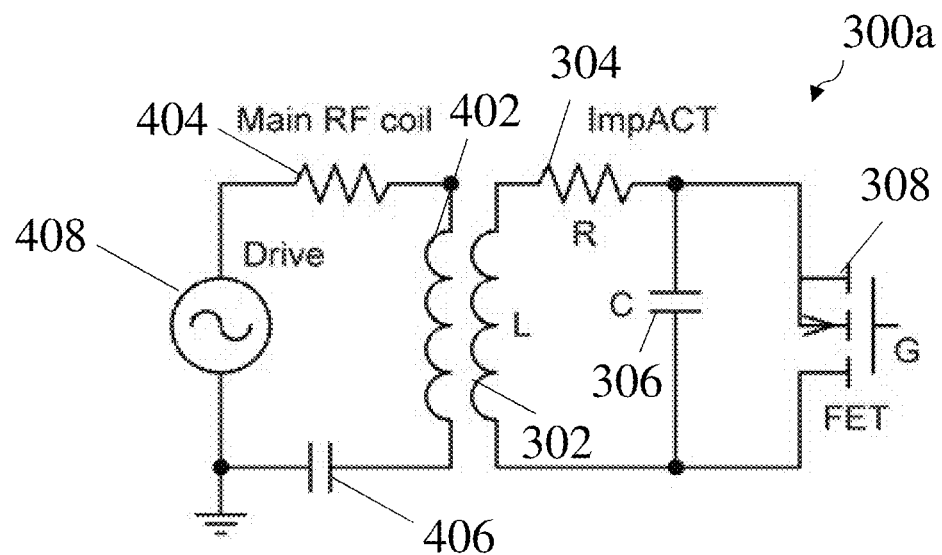
FIG. 4A is a circuit diagram showing the circuitry of FIG. 3A alongside MRI scanner circuitry.

FIGS. 4A-4E illustrate the theoretical performance of various possible implementations of a detector 100. FIG. 4A illustrates circuit 300a of FIG. 3A coupled to another circuit 400, which may function as an imaging device or sensor capable of producing and sensing varying magnetic fields coupled to detector (e.g., an MRI scanner). For example, resonant properties of the imaging device may be modeled by a resistor 404, inductor 402, and capacitor 406, with the inductor 402 serving as an antenna of the imaging device. A voltage source 408 (e.g., arbitrary waveform generator) may generate RF pulses to generate pulses emitted by the imaging device to drive the ensemble. Depending on a channel impedance state of the FET 308, coupling between the inductors 302 and 402 of the circuits 300a and 400 may be facilitated or interrupted. For example, coupling at the frequency of the signal generated by the voltage source 408, modeling the varying magnetic field of the imaging device, may be interrupted when the FET 308 closes due to a shift in resonant frequency of the circuit 300a when current is shunted from the capacitor 306 and/or inductor 302 to the FET 308.

Figure 4B:
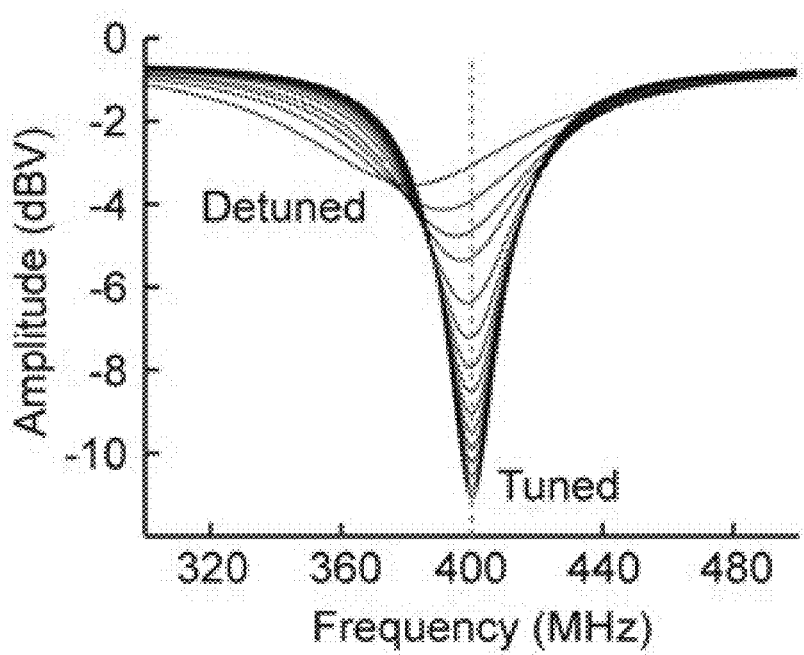
FIG. 4B is a line graph showing tuning curve simulations for the circuitry illustrated in FIG. 4A as a function of voltage input, according to one embodiment.

FIG. 4B shows tuning curve simulations as a function of voltage input to gate 108b of the FET 308 that causes the circuit 300a to vary between fully tuned and fully detuned states. As shown, the amplitude of the signal reflected back from the circuit 300a to the circuit 400 reaches a minimum at about 400 MHz in the tuned state, whereas a minimum in the detuned state is reached between 380 MHz and 400 MHz. The shifted minimum in reflected signal indicates that the resonant frequency of the circuit 300a is different in the tuned and detuned state. Notably, the minimum reflected signal content in the tuned state is less than −10 dBV, whereas the minimum reflected signal content in the detuned state is between −3.5 and −4 dBV. This is because the detuned circuit 300a reflects more of the signal back than the tuned circuit 300a.

Figure 4C:
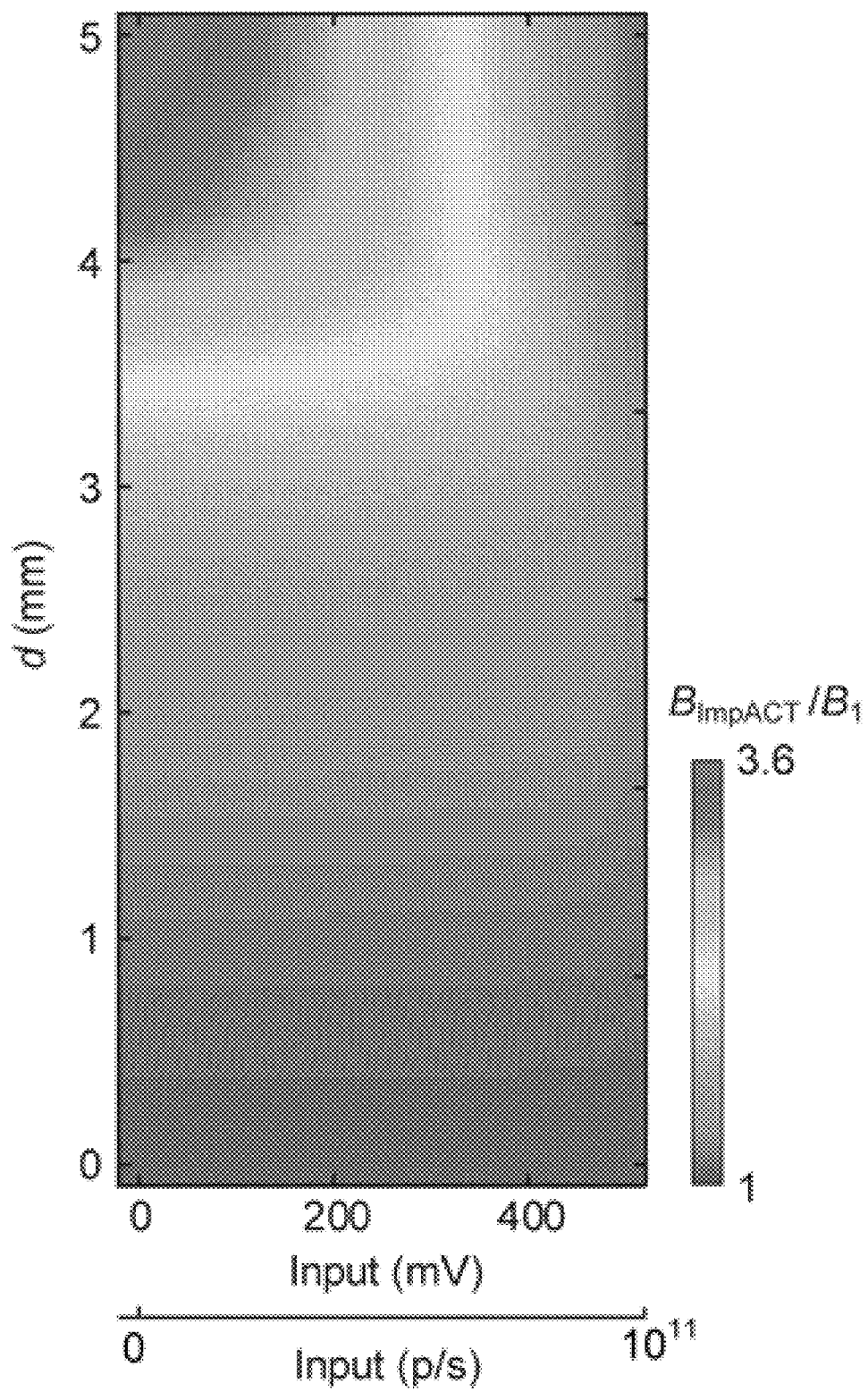
FIG. 4C is an intensity plot showing simulated relative enhancement of local RF amplitude corresponding to the circuitry of FIG. 4A as a function of the diameter (d) and gate input strength in mV or photons per second (p/s), according to one embodiment.

FIG. 4C shows simulated relative enhancement of local RF amplitude as a function of the diameter d of the inductor 302 of the circuit 300a and input strength in mV or photons per second (p/s). RF enhancement by the circuit 300a is expressed in terms of the ratio $B_{detector}/B_1$, which translates directly into an increase in flip angle during application of a pulse from circuit 400 (e.g., modeling an MRI pulse from the RF coil of an MRI scanner).

Figure 4D:
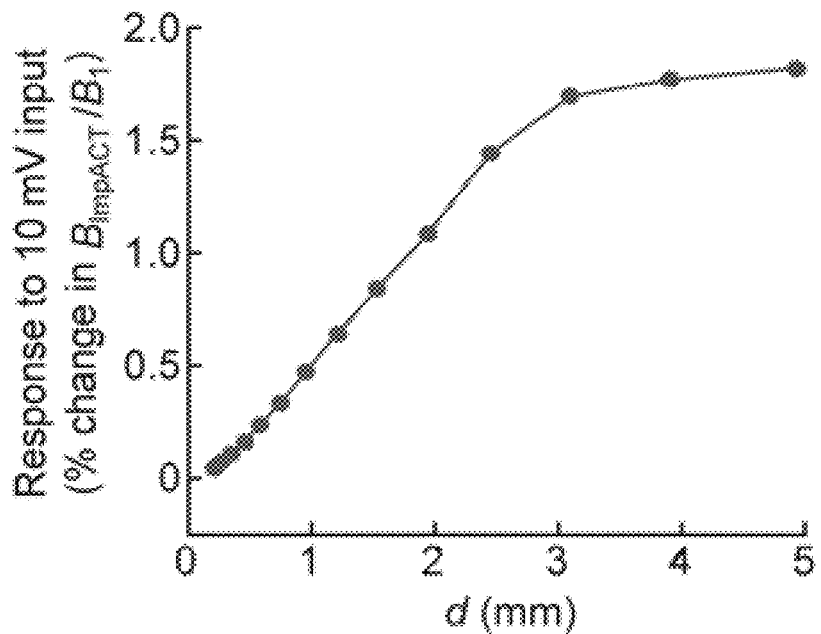
FIG. 4D is a line graph showing the response of the circuitry of FIG. 4A to a 10 mV gate input (also equivalent to $2 \times 10^9$ p/s) as a function of the detector diameter, according to one embodiment.
Figure 4E:
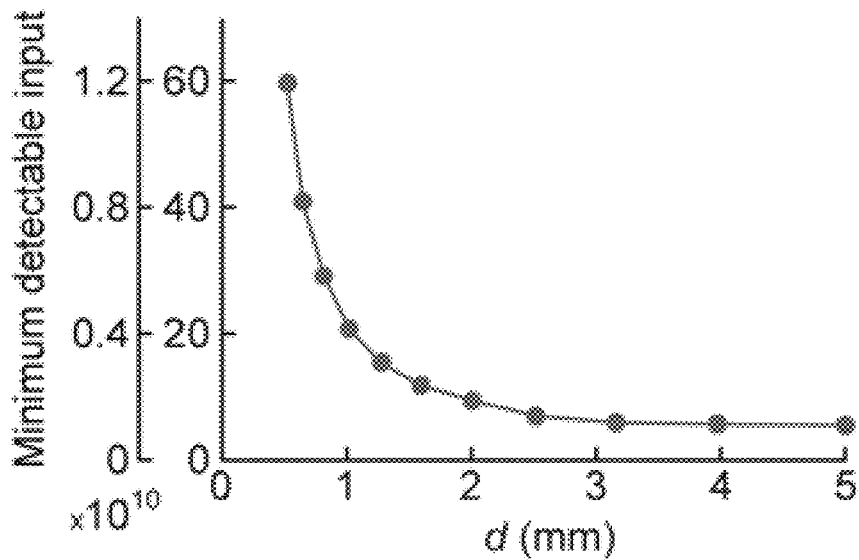
FIG. 4E is a line graph showing the minimum photonic and voltaic gate input signals to the circuitry of FIG. 4A predicted to produce 1% change or greater in the detector-to-MRI magnetic field ratio ($B_{ImpACT}/B_1$), as a function of device diameter.

FIGS. 4D-4E show simulated sensitivity of detectors 100 having various diameters d of the inductor 102. FIG. 4D shows the detector 100 response (in terms of the ratio $B_{detector}/B_1$) to a 10 mV input (also equivalent to $2\times10^9$ p/s) as a function of the diameter d of the inductor 102 of the detector 100. As shown in FIG. 4D, the percent change in $B_{detector}/B_1$ increases as the diameter d increases. Particularly, there is a roughly constant increase in percent change from less than 1 mm to 3 mm, after which the increase tapers off. For example, the percent change for a diameters of 1 mm, 2 mm, and 3 mm are about 0.5%, just over 1%, and about 1.75% for just over 3 mm. It should be appreciated that changes in $B_{detector}/B_1$ of 1% or greater are likely to be detectable in imaging. FIG. 4E shows the minimum detectable photonic and voltaic input signals simulated to produce a 1% change or greater in $B_{detector}/B_1$, as a function of the diameter d. As shown, the minimum detectable input decreases as the diameter d increases, which indicates that the voltage at the gate 108b of the FET 108 to change $B_{detector}/B_1$ in an amount detectable in imaging is smaller for larger diameter d.

Figure 5A:
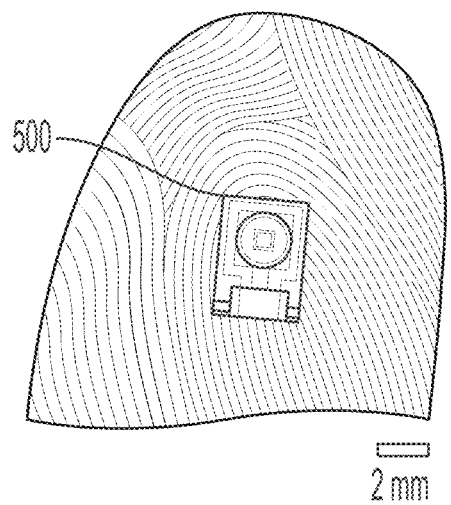
FIG. 5A illustrates a detector according to one embodiment fabricated using standard printed-circuit single turn inductors with 10 μm gold-plated copper as a thin film conductive layer and an inductor of diameter 3 mm, connected in parallel to FET sensor and a tuning component to enable initial resonance frequency at v=400 MHz.
Figure 5B:
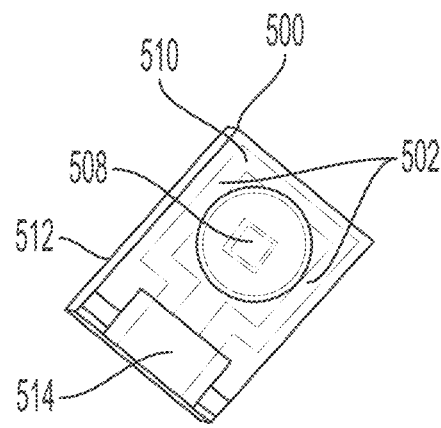
FIG. 5B is a close-up view of the detector of FIG. 5A, with components labeled.

FIGS. 5A-5E depict a device 500 including a detector as well as measured tuning and imaging performance of the device 500. FIGS. 5A-5B show the device 500 including the detector. FIG. 5A illustrates the device 500 on a human finger for size comparison, whereas FIG. 5B shows a close-up view of the device 500 for enhanced visibility. In the illustrated embodiment, the device 500 is fabricated using a standard printed-circuit single turn inductor 502 with 10 μm gold-plated copper as a thin film conductive layer 510 mounted on the circuit board 512. The inductor 502 has a diameter d of 3 mm connected in parallel to the FET 508 sensor and a capacitor 514 to enable an initial resonance frequency at μ=400 MHz.

FIG. 5C shows network analyzer measurements demonstrating tuning curves for the device 500 over various frequencies. For the measurements, a voltage input to a gate 508b of the FET 508 was swept from low $\Delta V_{GS}$ ($V_{GS}=V_{th}$) to high $\Delta V_{GS}$ ($V_{th}+1$ V), resulting in detuning of the detector 100 within device 500. More particularly, the detuning resulted in a 3.9-fold decrease of quality factor (Q) from 17.9 to 4.5, comparable to values of Q that were derived from the simulated tuning curves illustrated in FIGS. 4A-4E. FIG. 5D shows a more precise voltage sweep of the gate 508b of the FET 508 having millivolt-scale voltage inputs. More particularly, in FIG. 5D, the input voltage interval between adjacent curves is 10 mV. FIG. 5E shows the difference in MRI signals 530a and 530b by light-gated detuning of a photoFET-based detector juxtaposed to a water-based phantom. As shown, the MRI signal 530a in the absence of input is approximately 30% greater than in the presence of input indicated by the signal 530b.

FIGS. 6A-6G illustrate detector-mediated detection of bioluminescence in vitro and in vivo. FIG. 6A is a schematic of bioluminescence detection by a photosensitive detector circuit 600, which may be included in some embodiments of a detector. As indicated in FIG. 6A, a Luciferase (Luc) solution was used to stimulate bioluminescence. Luc in the presence of magnesium ions catalyzes the conversion of D-luciferin, ATP, and $O_2$ into oxyluciferin and light. The light acts on the gate terminal 608b of the photoFET 608, altering resonance properties of the circuit 600 and impacting coupling between the circuit 600 and a received MRI signal. FIG. 6B depicts percent change to an MRI signal measured using a 3 mm device including the photosensitive detector circuit 600 in the presence of 7.8 μM luciferase with 640a or without 640b addition of D-luciferin (DL). The percent changes reflect the percent difference from baseline image intensity distal to the detector. As shown, the DL addition results in a greater than 15% change in the MRI signal as compared to without the DL. FIG. 6C shows frequency response signal reflection measurements in the presence 642a and absence 642b of DL. As shown, minimum signal reflection with DL 642a occurs at a lower frequency than without DL 642b, and the minimum signal reflection level without DL 642b is lower than with DL 642a by at least 0.1 dBV, confirming the effect simulated in FIGS. 4B and 5C, namely, that light production affects the MRI signal by detuning the device. Error bars in FIGS. 6B-6C denote standard error of the mean (SEM) values (n=4).

Figure 6G:
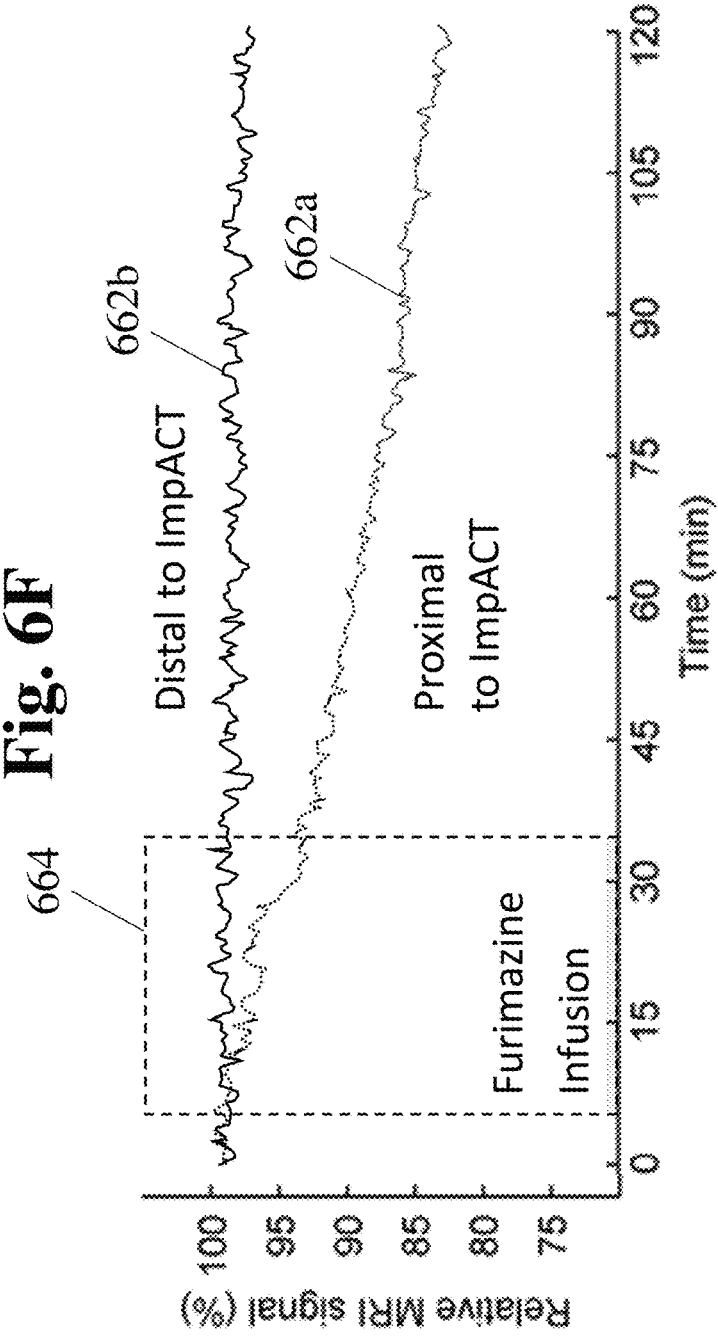
FIG. 6G shows mean time courses of relative MRI signals proximal and distal to the detector of FIG. 6D, according to one embodiment.
Figure 16:
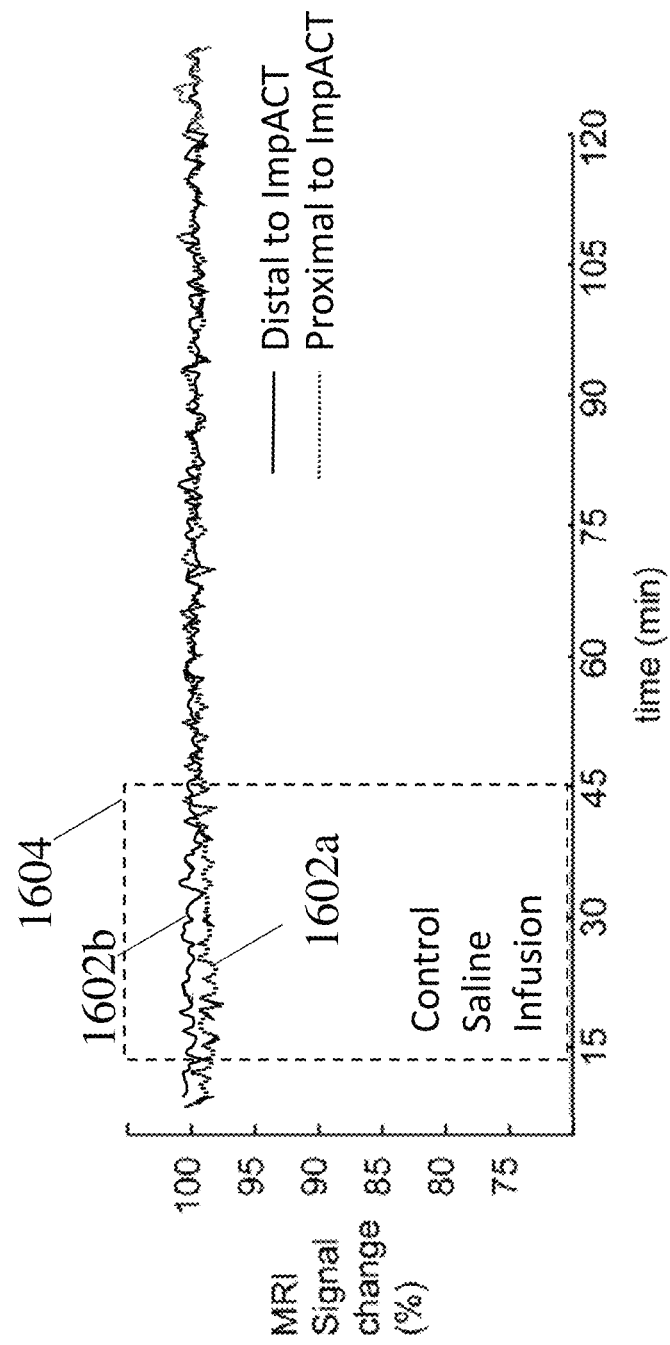
FIG. 16 illustrates MRI monitoring of the response of a detector to sham injections of saline in live rat brains, according to one embodiment.

FIGS. 6D-6G show MRI monitoring of bioluminescent cells in a live rat brain 650 by the detector circuit shown in FIG. 6A. Engineered luciferase (NanoLuc)-expressing HEK-293 cells were grafted into the cerebral cortex. A device 652 having the detector circuit 600 was implanted above the cells, and a cannula was inserted nearby for infusion of the NanoLuc substrate furimazine. FIG. 6D is a diagram illustrating the rat brain 650 with the device 652. FIG. 6E depicts an anatomical MRI scan of the rat-brain 650 showing the region of image signal modulated by the detector circuit 600. FIG. 6F-shows close-up MRI images obtained at t=0, 30, 60, 90 and 120 minutes before, during, and after furimazine infusion (t=5-35 mins). Signal enhancement 660 in the center of the images reflects the presence of the tuned detector device 650. The enhancement dims over time as the detector is progressively detuned by luminescence from the implanted cells. FIG. 6G shows mean time courses of relative MRI signals proximal 662a and distal 662b to the detector. The Furimazine infusion period 664 is indicated by the dashed line box. It should be appreciated that control experiments with injections lacking furimazine, described herein including with reference to FIG. 16, showed no discernable signal changes.

Figure 7:
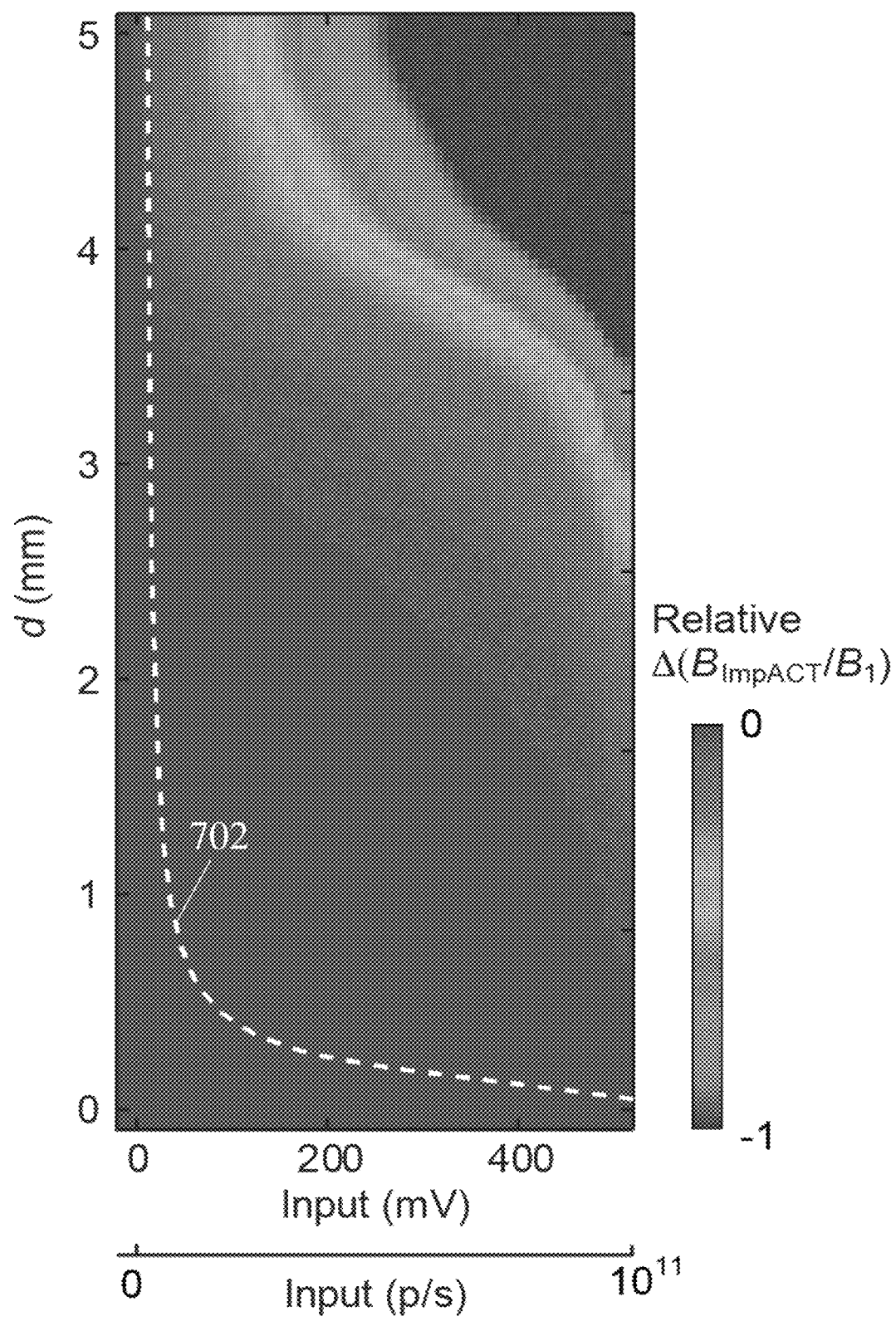
FIG. 7 is an intensity chart showing the measured relative change in enhancement of local RF field intensity as a function of dimensions and gate input strength for a detector, according to one embodiment.

FIG. 7 shows the measured relative change in enhancement of local RF field intensity in terms of the ratio $B_{detector}/B_1$ as a function of diameter d of the detector and the amplitude of signals applied to the gate of the FET. In FIG. 7, MRI effects are modeled as enhancements Δ

($B_{detector}/B_1$) to the local RF field in the neighborhood of the detector, normalized to the full range of the ratio, in response to different input amplitudes in mV or p/s, plotted on the horizontal axis, and as a function of diameter d on the vertical axis. The white dashed line 702 denotes the minimum input voltage to produce 1% changes in $B_{detector}/B_1$.

FIGS. 8A-8B show enhancement of local RF intensity in terms of $B_{detector}/B_1$ as a function of the thickness of the conductive film and the amplitude of the input voltage applied to the gate of the FET. In FIG. 8A, MRI effects are modeled as enhancements to the local RF field in the neighborhood of the detector, as a function of the conductive film thickness ($t_m$) of the detector and the input strength in mV or p/s applied to the gate, assuming a diameter of d=3 mm. For conductive film thickness $t_m<8$ μm, the difference between enhancements to MRI signals in the low and high gate input states decreases rapidly, and for conductive film thickness $t_m<1$ μm, the enhancement falls below the estimated detection limit of 1% change in $B_{detector}/B_1$ for the entire gate input voltage range. This sets a lower bound on conductive film thickness $t_m$ for constructing effective detectors in some embodiments, depending on the specific varying magnetic field applied. FIG. 8B illustrates the same results shown as relative change in local field enhancement $\Delta(B_{detector}/B_1)$. The white dashed line 802 denotes minimum gate input voltage to produce 1% changes in $B_{detector}/B_1$.

Figure 9A:
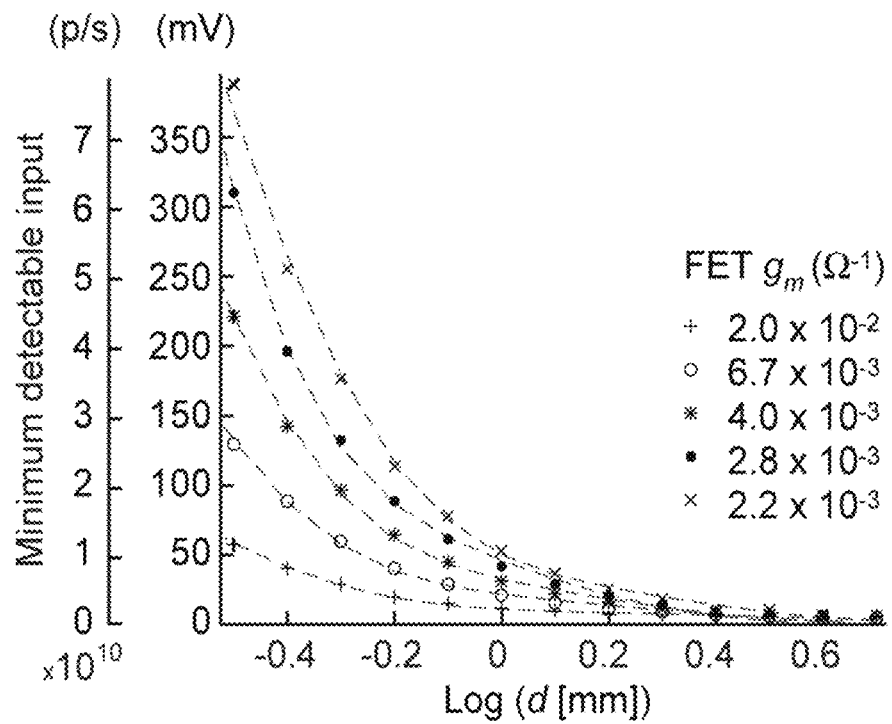
FIG. 9A is a line graph showing a range of gate input sensitivities for various detectors having diameters d=0.3 to 4 mm, according to one embodiment.
Figure 9B:
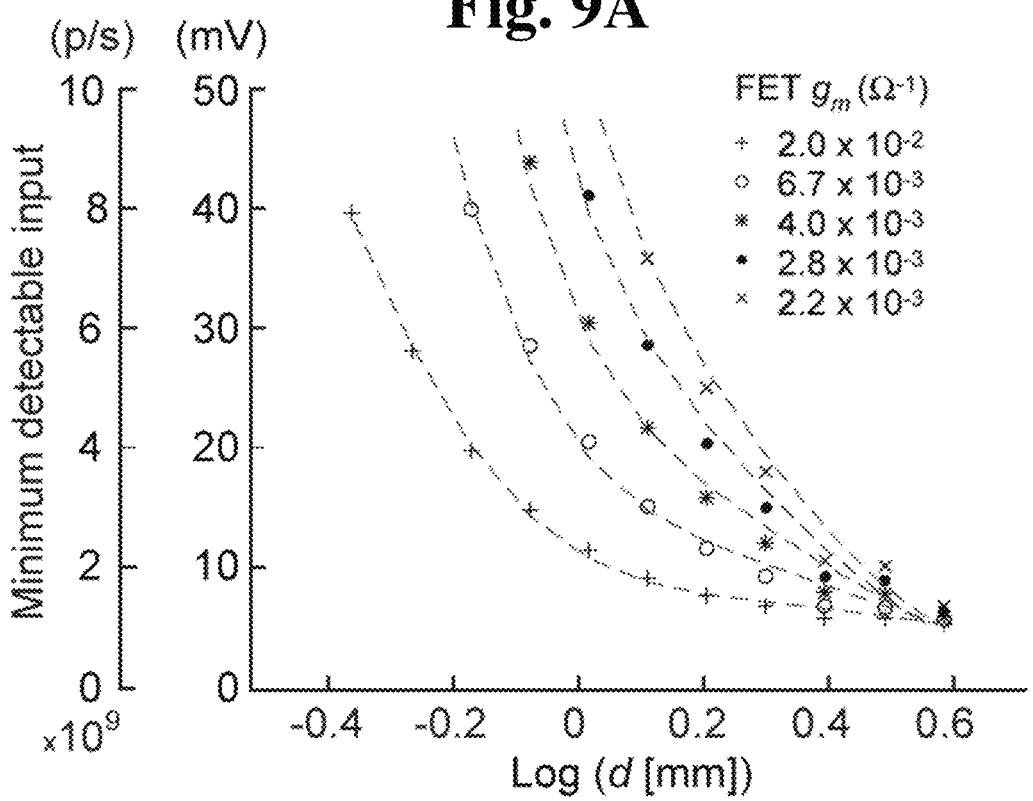
FIG. 9B is a line graph depicting the same data as FIG. 9A, zoomed in to emphasize gate input sensitivities in the 0-50 mV (0-$10^{10}$ p/s) range, according to one embodiment.

FIGS. 9A-9B show sensitivity of a detector as a function of the diameter d for various transconductance configurations of the FET. In FIGS. 9A-9B minimum photonic and voltaic input signals to the gate predicted to produce 1% change or greater in $B_{detector}/B_1$ were computed as a function of device diameter (d) for various transconductance ($g_m$) values shown. FIG. 9A shows the full range of sensitivities for devices of d=0.3 to 4 mm, whereas FIG. 9B depicts the same data, zoomed in to emphasize sensitivities in the 0-50 mV (0-$10^{10}$ p/s) gate voltage input range.

Figure 10:
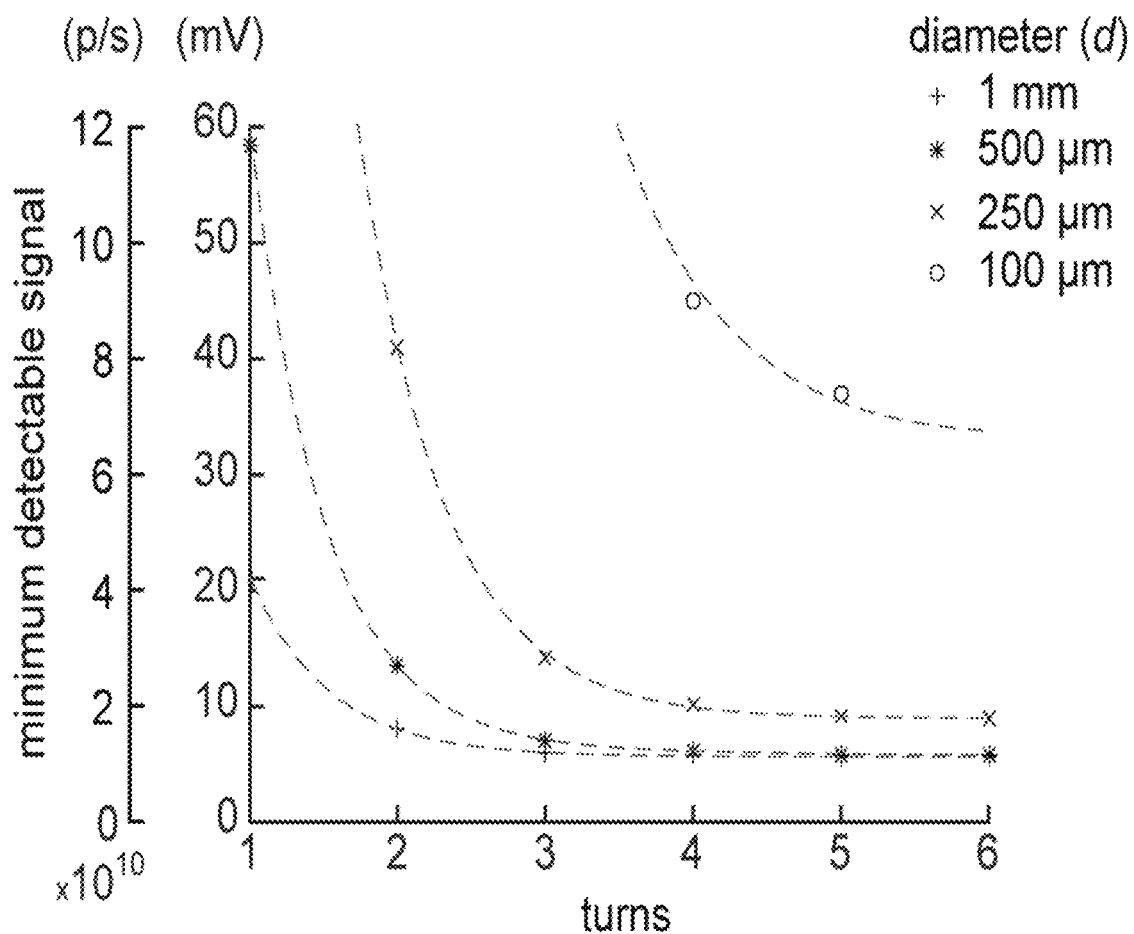
FIG. 10 is a line graph showing sensitivity of submillimeter multiturn detectors to voltaic and photonic gate inputs, according to one embodiment.

FIG. 10 shows sensitivity of a submillimeter multiturn embodiment of a detector to voltaic and photonic inputs at a gate of the FET. As shown in FIG. 10, embodiments with diameters d of 1 mm, 500 μm, 250 μm, and 100 μm, can achieve 1% changes in $B_{detector}/B_1$ in response to inputs of −5.6 mV, −5.8 mV, −9.9 mV, and −33 mV, respectively.

FIGS. 11A-11B show sensitivity of a detector to biologically relevant fields.

Initially, a detector 100 is tuned to a resonance frequency of 400 MHz with a gate input voltage suitable to achieve the closed state of the FET, and is detuned by an input voltage at the gate suitable to change the conducting state of the FET. FIG. 11A shows that the application of voltage above $V_{th}$ to the gate detunes the detector and decreases Q, causing a reduction of MRI signal intensity depicted in the corresponding images. $\Delta V_{GS}$ values are shown for each condition, and the 400 MHz frequency is denoted by vertical dotted lines in each tuning curve graph. FIG. 11B shows that photonic input from 0-$10^{13}$ p/s into a photoFET-based detector produces similar responses as the voltage input in panel (a).

Figure 12A:
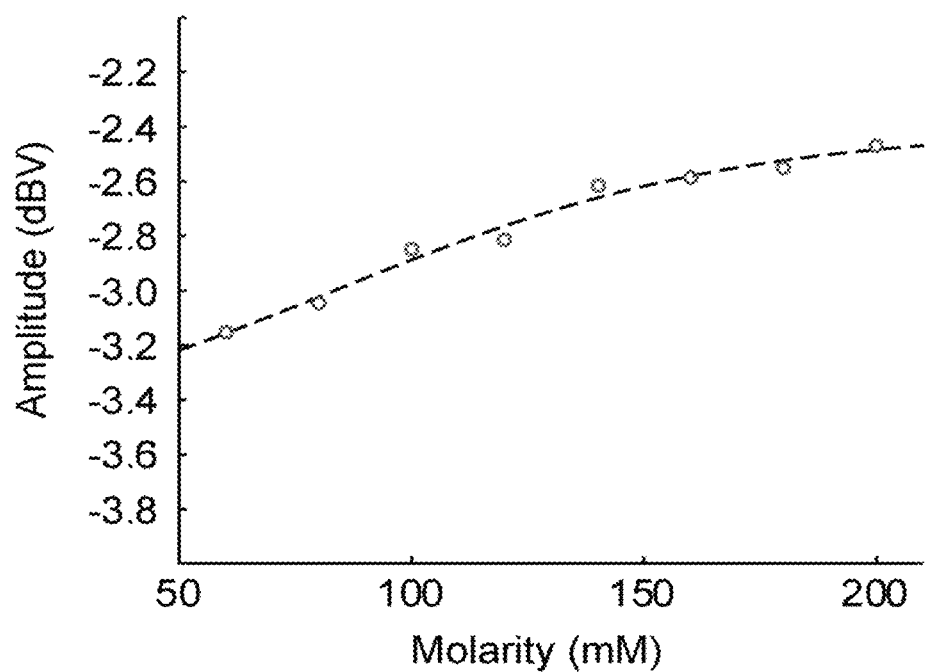
FIG. 12A is a line graph depicting experimentally-determined dependence of a detector on ionic strength, according to one embodiment.
Figure 12B:
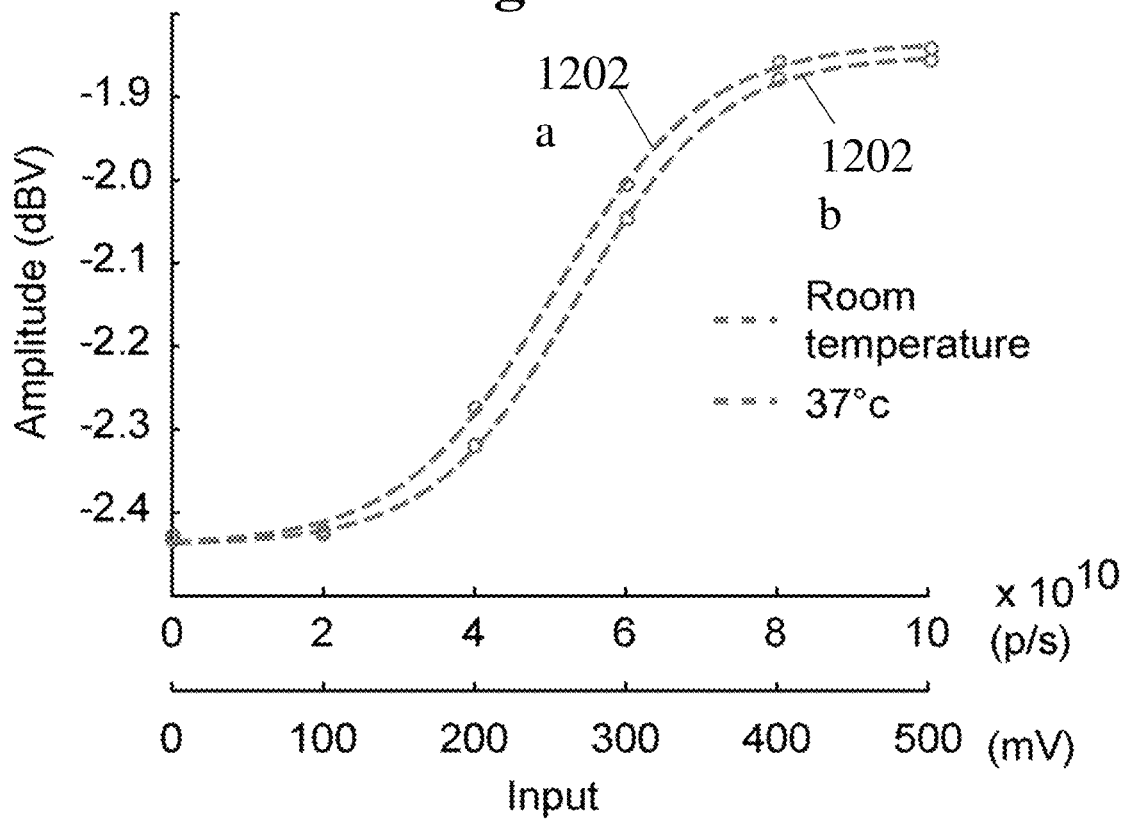
FIG. 12B is a line graph depicting temperature-dependence of responses of a detector to stimulation, measuring tuning behavior against a 150 mM saline sample across the dynamic range of gate inputs at room temperature 22° C. and 37° C., according to one embodiment.
Figure 12C:
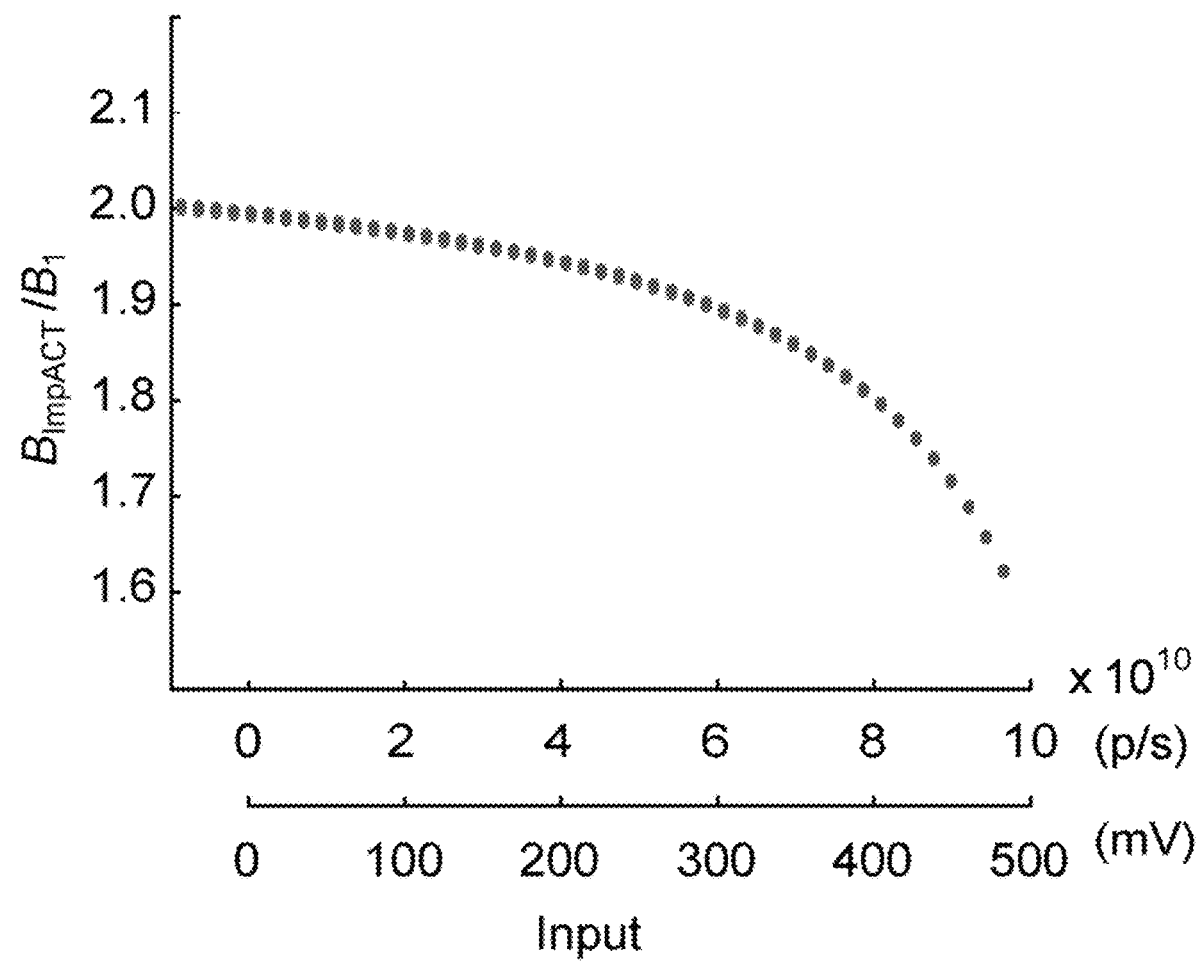
FIG. 12C is a line graph depicting simulated response profiles for a detector predicted for operation at small frequency offsets from a main field resonance frequency of 400 MHz, according to one embodiment.

FIGS. 12A-12C show detector sensitivity to various environmental changes. FIG. 12A depicts experimentally-determined dependence on ionic strength. A 3 mm diameter embodiment of a detector was initially tuned to a resonance frequency of 400 MHz and juxtaposed to saline solutions of 60-200 mM. The graph in FIG. 12A shows tuning depth (dBV) at the resonance frequency for different molarity values. FIG. 12B illustrates temperature-dependence of the detector sensitivity to stimulation in terms of gate input voltage. Tuning behavior against a 150 mM saline sample was measured across the entire dynamic range of inputs at room temperature 1202a and 37° C. 1202b. FIG. 12C shows simulated detector response profiles predicted for operation at small frequency offsets from the main field resonance frequency of 400 MHz. Curves determined over a range of offsets from 399 to 401 MHz are superimposed, showing the negligible effect of realistic field distortions of up to 2,500 parts per million.

Figure 13B:
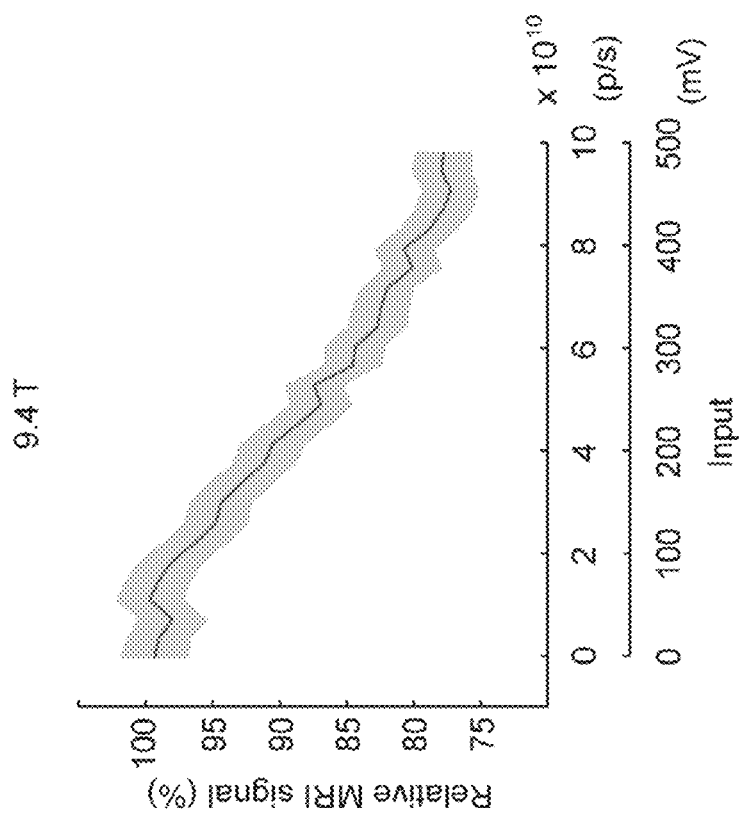
FIG. 13B shows the measured change in relative MRI signals corresponding to the a detector tuned to 400 MHz and operated on a 9.4 T scanner over a range of gate input voltage amplitudes, according to one embodiment.
Figure 13A:
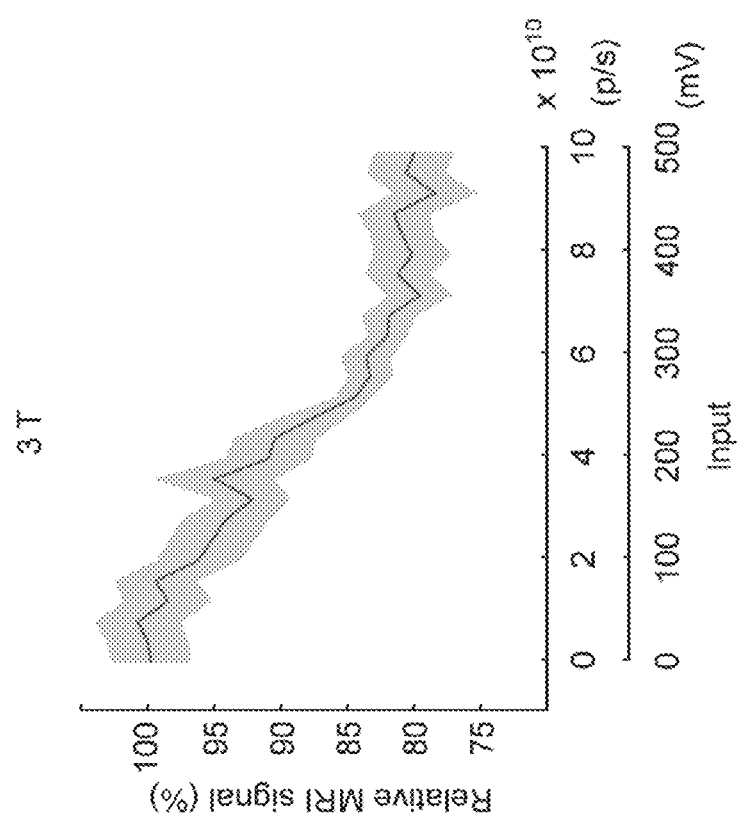
FIG. 13A shows the measured change in relative MRI signals corresponding to a 3 mm diameter detector tuned to v=123.2 MHz and operated in a 3T clinical scanner over a range of gate input voltage amplitudes, according to one embodiment.
Figure 13C:
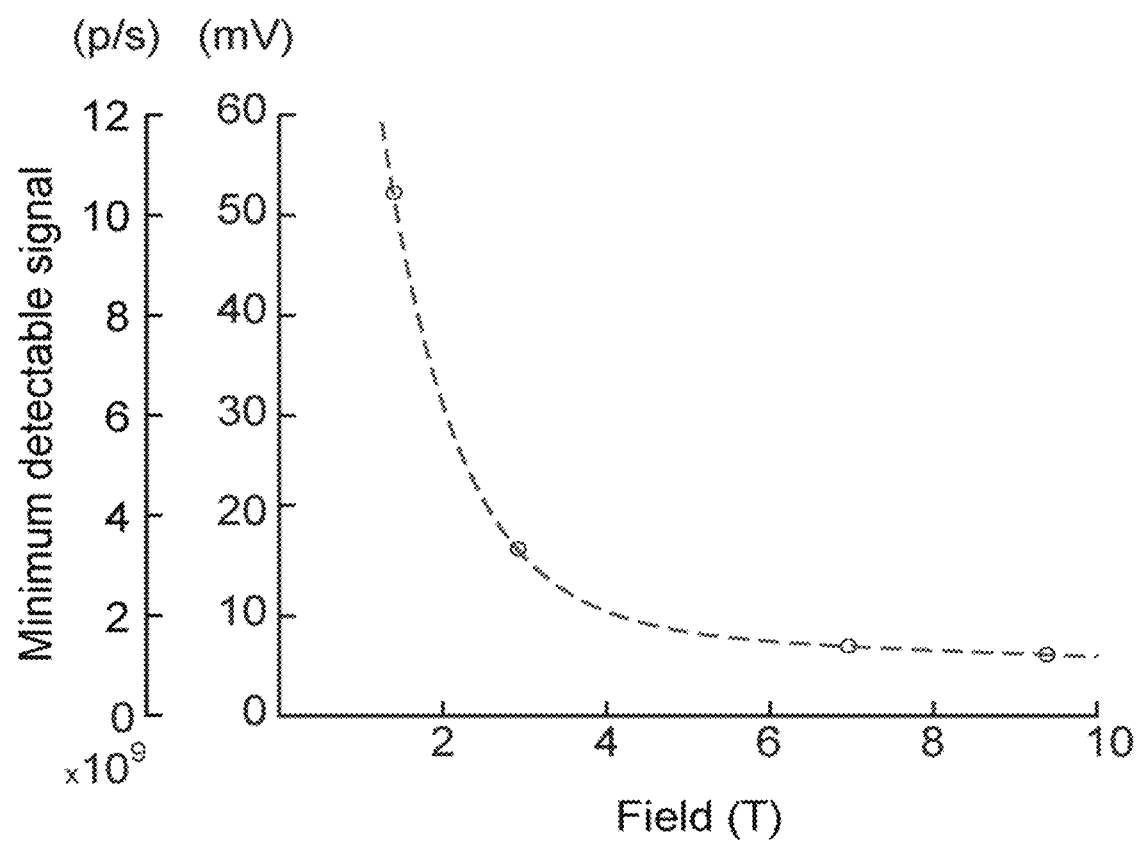
FIG. 13C is a line graph showing simulated sensitivity of a detector, defined as the gate input voltage amplitude predicted to produce a 1% change in the detector/MRI field ratio $B_{ImpACT}/B_1$, plotted against multiple magnetic field strengths in T, according to one embodiment.

FIGS. 13A-13C show detector sensitivity at different MRI $B_0$ field strengths. FIG. 13A shows that a 3 mm diameter embodiment of a detector tuned to a resonant frequency of 123.2 MHz and operated in a 3 Tesla (T) clinical scanner over the full range of gate input voltage amplitudes. FIG. 13B shows that an embodiment of a detector tuned to a resonant frequency of 400 MHz was similarly operated on a 9.4 T scanner. Shading denotes SEM over 8 voxels in proximity to the detector. FIG. 13C shows simulated sensitivity of a detector in terms of gate input voltage amplitude sensitivity predicted to produce a 1% change in $B_{detector}/B_1$, as a function of magnetic field strength in T.

Figure 14:
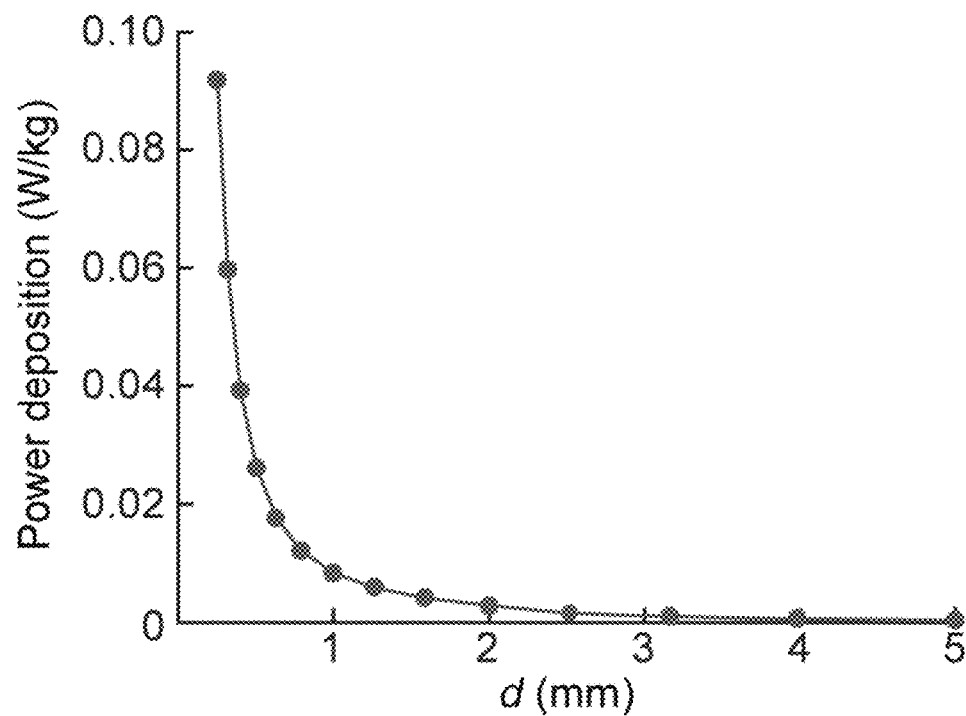
FIG. 14 is a line graph illustrating estimated maximum local specific power deposition by a detector, according to one embodiment.

FIG. 14 illustrates maximum local specific power deposition by detectors having various diameters d. For detectors 100 of different diameters d, an upper bound on the local specific absorbance rate was calculated by computing the maximum specific power deposited in the detector, and then assuming that this power is transferred to a spherical volume of tissue of twice the diameter d of the detector. The depicted spherical volumes correspond to deployment of multiple detectors with a pitch distance of at least d (e.g. the detectors are one diameter apart at the least). This volume was chosen conservatively to reflect the maximal density at which multiple functional detectors could be spaced in tissue, with a separation of twice their diameter d minimizing the potential for electromagnetic coupling between the detectors. In most applications, the inter-detector spacing and corresponding volumes of power dissipation are likely to be much greater.

Figure 15:
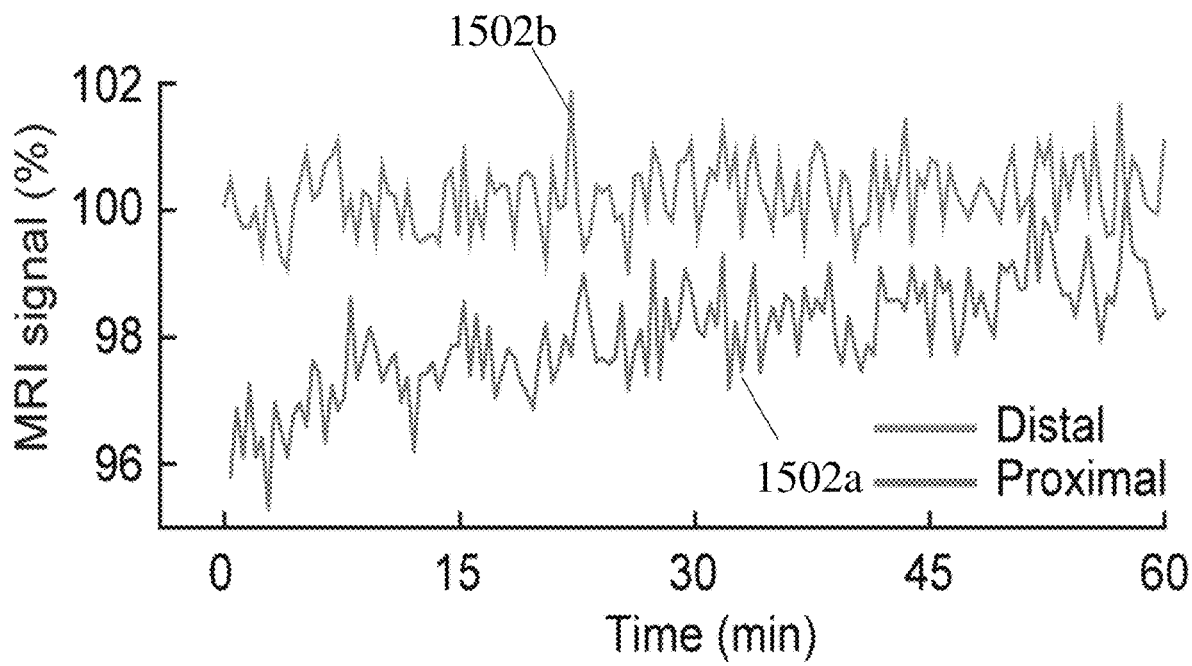
FIG. 15 is a line graph showing time course of relative MRI signal produced by NanoLuc-expressing HEK293 cells in close juxtaposition to a detector following addition of 5 µM furimazine, according to one embodiment.

FIG. 15 shows time course of relative MRI signal produced by NanoLuc-expressing HEK293 cells in close juxtaposition to a detector, following addition of 5 μM furimazine. Signals close to the device 1502a show relative suppression due to detuning of the device compared with distal MRI signals 1502b, which are not affected by the detector or its tuning status.

FIG. 16 illustrates MRI monitoring of control experiments in which a detector circuit responds to sham injections of saline in live rat brains. The control experiments were performed as in FIG. 6G, but with injection of saline solution instead of furimazine. Engineered luciferase (NanoLuc)-expressing HEK-293 cells were grafted into the cerebral cortex and a detector having the detector circuit illustrated in FIG. 6A was implanted above the cells. An infusion cannula was inserted nearby for infusion of saline. Saline infusion (t=5-35 mins) resulted in no significant signal enhancement in the center of the detector (p=0.9309) which remained tuned throughout the experiments. Mean time course depicts relative MRI signal detected both proximal 1602a and distal 1602b to the detector. The saline infusion period is indicated by the dashed line box 1604. Signal change axis spans 70-100% as in FIG. 6G.

Figure 17A:
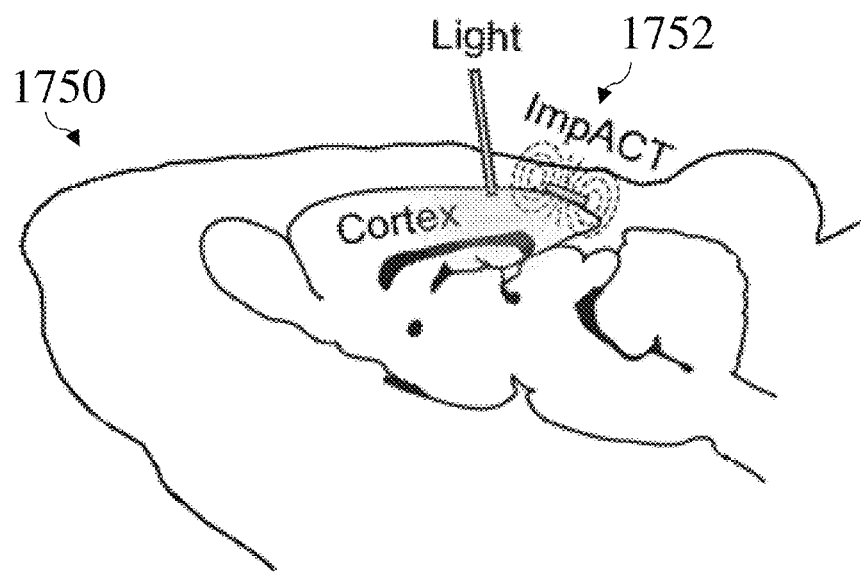
FIG. 17A is a schematic showing a 3 mm diameter photosensitive detector implanted above the cortical surface of an anesthetized rat and an optical fiber inserted 1 mm anterior to implantation site for light-dependent modulation, according to one embodiment.
Figure 17B:
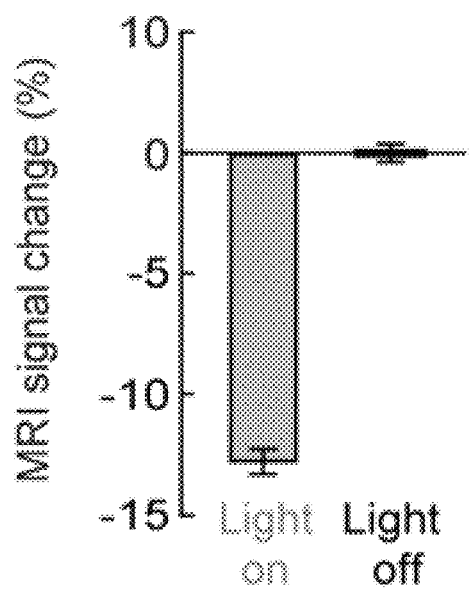
FIG. 17B is a bar graph showing the application of $5 \times 10^{10}$ p/s generated MRI signal decrease of 12.7±0.7% in cortical region proximal to a detector, according to one embodiment.
Figure 17C:
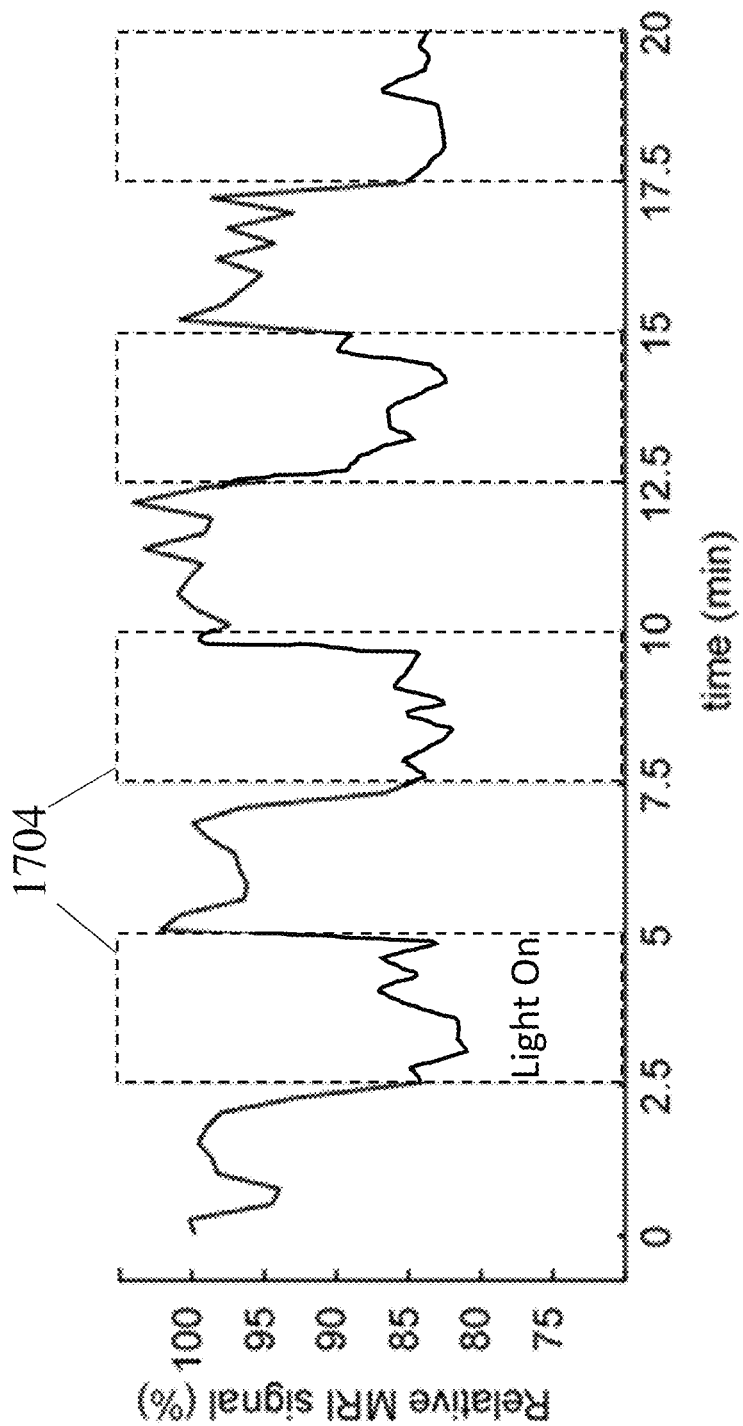
FIG. 17C is a line graph showing relative MRI signal proximal to a detector in response to intermittent application of $5 \times 10^{10}$ p/s through the optical fiber, according to one embodiment.

FIGS. 17A-17C show reversible detuning of a detector in live rat brain 1750. FIG. 17A shows that a device 1752 including a 3 mm diameter d photosensitive detector was implanted above the cortical surface of an anesthetized rat and an optical fiber was inserted 1 mm anterior to implantation site for light-dependent modulation. FIG. 17B shows the application of $5 \times 10^{10}$ p/s generated MRI signal and the corresponding decrease of 12.7±0.7% in cortical region proximal to the device, with error bars indicating SEM over four experiments. FIG. 17C shows relative MRI signal proximal to a detector in response to intermittent application of $5 \times 10^{10}$ p/s through the optical fiber. Dashed box areas 1704 denote 5 min epochs of light application.

According to some embodiments of a detector 100, the diameter d of the device could be 1 μm and above. However, thicknesses of less than or equal to 1 cm, less than or equal to 8 mm, less than or equal to 6 mm, less than or equal to 4 mm, less than or equal to 2 mm, less than or equal to 100 μm, less than or equal to 50 μm, less than or equal to 25 μm, less than or equal to 20 μm, less than or equal to 15 μm, less than or equal to 10 μm, less than or equal to 5 μm, less than or equal to 1 μm, less than or equal to 0.9 μm, less than or equal to 0.8 μm, less than or equal to 0.7 μm, less than or equal to 0.6 μm, or less than or equal to 0.5 μm, are also possible. In some embodiments, the thickness is greater than or equal to 0.5 μm, greater than or equal to 0.6 μm, greater than or equal to 0.7 μm, greater than or equal to 0.8 μm, greater than or equal to 0.9 μm, greater than or equal to 1 μm, greater than or equal to 5 μm, greater than or equal to 10 μm, greater than or equal to 15 μm, greater than or equal to 20 μm, greater than or equal to 25 μm, greater than or equal to 50 μm, greater than or equal to 100 μm, greater than or equal to 2 mm, greater than or equal to 4 mm, greater than or equal to 6 mm, greater than or equal to 8 mm, or greater than or equal to 71 cm. Combinations of the above-referenced ranges are also possible (e.g., greater than or equal to 1 μm and less than or equal to 1 cm).

According to some embodiments of a detector, the diameter d of the inductor could be 5 mm. However, diameters of less than or equal to 1 cm, less than or equal to 9 mm, less than or equal to 8 mm, less than or equal to 7 mm, less than or equal to 6 mm, less than or equal to 5 mm, less than or equal to 4 mm, less than or equal to 3 mm, less than or equal to 2 mm, less than or equal to 1 mm, less than or equal to 900 μm, less than or equal to 800 μm, less than or equal to 700 μm, less than or equal to 600 μm, less than or equal to 500 μm, less than or equal to 400 μm, less than or equal to 300 μm, less than or equal to 200 μm, or less than or equal to 100 μm, are also possible. In some embodiments, the diameter is greater than or equal to 100 μm, greater than or equal to 200 μm, greater than or equal to 300 μm, greater than or equal to 400 μm, greater than or equal to 500 μm, greater than or equal to 600 μm, greater than or equal to 700 μm, greater than or equal to 800 μm, greater than or equal to 900 μm, greater than or equal to 1 mm, greater than or equal to 2 mm, greater than or equal to 3 mm, greater than or equal to 4 mm, greater than or equal to 5 mm, greater than or equal to 6 mm, greater than or equal to 7 mm, greater than or equal to 8 mm, greater than or equal to 9 mm, or greater than or equal to 1 cm. Combinations of the above-referenced ranges are also possible (e.g., greater than or equal to 100 μm and less than or equal to 1 cm).

While the depicted embodiments show the detectors being used within well-known closed MRI machines, it should be understood that the teachings of the current disclosure can be applied with any RF coils producing a magnetic field of any magnitude sufficient to produce detectable resonance in the detectors. It should be understood that as technology progresses, the possible magnitudes of detectable field strength will change, but the teachings of the current disclosure should still be applicable.

Example: Experimental Overview and Methodology

The design parameters relevant to construction of detectors on millimeter and submillimeter scales were explored, and in vivo functionality of a detector were demonstrated for measuring time-resolved bioluminescence in rodent brain. As detailed below, the experimental testing confirms the disclosed detectors and associated methods offer a versatile avenue for biophysical sensing using microcircuits that leverage the potent capabilities of MRI. Additionally, a minimally-invasive technology for improved measurement of optical signals near their origin could vastly expand the range of physiological phenomena accessible to monitoring. The present disclosure provides valuable tools for basic research in neuroscience and biomedical imaging enabling new types of assays and protocols for physiology studies, drug testing, and may prove useful for clinical diagnostic purposes.

Example: Theoretical Characteristics

To explore the potential of detectors to sense biologically-relevant signals, their predicted responses were modeled to realistic biophysical signal sources. Biophysical potentials range from tens to hundreds of microvolts in the case of neuronal extracellular field potentials, and reach tens of millivolts in the case of muscle contraction, cardiac activity, neuromuscular synaptic events, and oscillations in the central nervous system. Meanwhile, photonic signals generated by luminescent cell lines and animal models attain flux values of $10^{10}$ photons per second (p/s) or more, depending on which luminescent reporter is used and on the factors regulating its activity. To test the prospects for detecting such signals, the response of the devices were simulated as a function of three key parameters: (1) the input signal introduced at the FET gate electrode, simulated as a change in the source-drain conductance of the FET due to alteration of its gate-source voltage ($V_{GS}$) or to photonic input when using a photosensitive FET (e.g., photoFET); (2) the diameter d of the detector's inductor, which determines its overall size; and (3) the thickness of the metal film ($t_m$) used in the detector circuitry.

The simulation model consisted of a circuit 300a equivalent to the detector inductively coupled to a circuit 400 representing a typical transmit-receive MRI volume coil (FIG. 4A). The detector frequency response is measured as a tuning curve—the graph of the RF signal reflected from the inductor 402 (e.g., modeling the MRI RF coil), versus transmission frequency (FIG. 4B). The minimum of the curve indicates the detector's tuning frequency v, and the ratio of this frequency to the full width at half height of the curve is the device's quality factor Q. The detector transmits greatest power when Q is maximized and the resonant frequency of the detector matches that of the MRI RF transmit-receive coil. In the simulations, the detector is initially tuned to the resonance frequency of v=400 MHz, corresponding to an MRI operating magnetic field strength $B_0$ of 9.4 T. Opening the FET 308 (or photoFET in some embodiments) thus detunes the circuit 300a, or other appropriate detection circuit. Response properties of these active elements were assumed to follow typical current-voltage characteristics, and were set according to specifications of sensitive, commercially available FET devices used in subsequent experiments. The source-drain resistance across the transistor falls from a value of 5 kΩ in the FET's closed state to a value of 0.2 kΩ in the FET's open state. Transitions between these values occur over an interval ranging between $\Delta V_{GS}$=0 to 500 mV, where $\Delta V_{GS}$ is the difference between $V_{GS}$ and the threshold voltage for FET opening, $V_{th}$.

FIG. 4B illustrates the shift in the tuning curve as a function of $\Delta V_{GS}$ for a representative simulation of a detector with single-turn inductor diameter d=10 mm and $t_m$=10 µm. The tuned curve (low $\Delta V_{GS}$) displayed Q of 17.7, while the detuned curve (high $\Delta V_{GS}$) displayed a Q of 4.5. This corresponds to an input-dependent 8.6 dBV (2.7-fold) change in transmission efficiency through the detector.

Example: Expected Dynamic Range and Sensitivity in MRI

To predict how detector tuning changes would be likely to affect actual MRI signals, the simulation approach was used to estimate the strength of the local RF field induced in the detector by the RF coil in a realistic imaging scenario. The ratio of the detector's local field ($B_{detector}$) to the field strength produced by the scanner's RF coil ($B_1$) provides an approximate measure of the local MRI signal amplification expected at the detector location (see Methods, discussed herein below).

FIG. 4C depicts $B_{detector}/B_1$ as a function of voltage or photonic input amplitude for detectors with a range of diameters and $t_m$=10 µm. For detectors with diameters d=1, 3, and 5 mm, values of $B_{detector}/B_1$ were 1.5, 2.0, and 3.5, respectively, in the fully tuned state and 1.4, 1.6, and 1.4 in the fully detuned states, reflecting a strong size dependence of device performance characteristics. These values correspond to stimulus-dependent modulation by up to 60% for the largest devices across the full range of input strengths (FIG. 7). For each detector, changes in $B_{detector}/B_1$ are approximately linearly proportional to inputs in the 0-300 mV range, also equivalent to luminescent inputs of 0-1.7× $10^{10}$ p/s falling on the 0.09 mm² photoFET light sensor that were modeled. For gate voltage inputs greater than 300 mV or 1.7×$10^{10}$ p/s, the predicted detector responses become increasingly nonlinear; they reach an asymptote by input levels of 500 mV or $10^{11}$ p/s, at which point the FET or photoFET component is fully open and the detector cannot be further detuned. These input levels thus establish an upper bound on the dynamic range of the devices.

To estimate detector responses to small biological-scale inputs, the modulations in $B_{detector}/B_1$ were expected to arise from inputs of 10 mV or 2×$10^9$ p/s (FIG. 4D). For detectors with d=0-3 mm, the modeled signal change varies linearly in proportion to detector size. For diameter d above d=3 mm, sensitivity to 10 mV gate input voltage reaches a plateau, with expected modulations of about 1.6% in $B_{detector}/B_1$. The minimum detectable detector input was also estimated, operationally defined as the voltage or photonic amplitude required to produce a 1% change in $B_{detector}/B_1$ from its base value (FIG. 4E). This definition was justified by the fact that functional MRI experiments commonly detect imaging signal changes of about this magnitude or larger. Based on this criterion, it was predicted that a 5 mm diameter d, single-turn detector could sense inputs as low as 5.4 mV, comparable to extracellular electrical potentials, and that a 1 mm device could sense inputs of at least 20.8 mV, comparable to transmembrane voltages in single cells. Detectors of diameter d=1 mm and d=5 mm could also detect photonic inputs of 4.2×$10^9$ p/s and 1.1×$10^9$ p/s, respectively. With changes to the metal layer thickness, FET transconductance, and number of turns, additional sensitivity improvements or reductions in device dimensions could be possible. Sensitivity to gate input voltages below 10 mV are predicted for multi-turn detectors as small as 250 µm in diameter d (see Additional detector design considerations below and FIGS. 8A-8B, 9A-9B, and 10).

Example: Validation of in MRI

In order to validate the simulations and verify the ability of an actual detector to undergo stimulus-dependent changes in tuning in an experimental setting, a series of single-turn thin film FET-gated circuits were constructed. A device with d=3 mm and $t_m$=10 µm is depicted in FIG. 5A and diagrammed in FIG. 5B. A second detector with dimensions matching the model parameters of FIG. 4B (diameter d=10 mm) was used for experimental validation of the predicted tuning behavior. Using a network analyzer inductively coupled to the device, the frequency response was measured over a range of $\Delta V_{GS}$ values (FIG. 5C). Behavior of this detector closely paralleled the simulated results, with Q values of 17.9 and 4.5 in the fully tuned and detuned states, respectively, almost exactly matching the model calculations. To probe the sensitivity of the device, the detector's response to the millivolt-scale inputs most relevant to biophysical phenomena were then examined. Inputs with $\Delta V_{GS}$=0-90 mV in 10 mV increments all produced discernible changes in the detector tuning curve (FIG. 5D). The responses are equivalent to an average change in reflected amplitude by 0.61±0.11 dBV per 10 mV input increment, indicating that millivolt-scale inputs are easily detectable.

The performance characteristics indicated by the tuning curves of FIG. 5C-5D apply to behavior of detectors during steady-state RF irradiation, but imaging applications would require the detector to be functional during highly transient RF pulses typical of MRI scanner operation. In order to test the detector's functionality and sensitivity in imaging, MRI of FET and photoFET-based detectors were performed during modulation of their voltage or photonic gate input. The detectors were placed inside a 78 mm diameter MRI transmit-receive coil while a simple MRI gradient echo pulse sequence with excitation pulse width of 1 ms and flip angle 30° was applied. Parallel changes in tuning and image intensity could be obtained across wide dynamic ranges, using both types of input (FIGS. 11A-11B). Representative results obtained using a photo-sensitive detector constructed with diameter d=3 mm and $t_m$=10 µm are shown in FIG. 5E. The device was tuned to the MRI scanner's operating frequency of 400 MHz in the absence of input; in this condition, the MRI signal proximal to the inductor element of the circuit was 30.4±4.7% higher than the water signal distal to the device, reflecting local intensification of RF flux by the detector in its tuned state. When an input of 1×$10^{11}$ p/s was applied, the MRI signal enhancement near the detector diminished to only 5.6±2.7% over baseline, a significant input-dependent decrease (t-test p<0.005 over the n=8 closest image pixels).

To examine the likely specificity of the disclosed detector-mediated MRI signal to input-dependent modulations, the detector's sensitivity to the extraneous environmental factors that could vary in realistic contexts was examined. In order to quantify the effect of ion concentration in the vicinity of the 3 mm detector, measurements were performed over a range of buffer dilutions (FIG. 12A). The results indicate that at salt concentrations relevant to serum or cerebrospinal fluid (150 mM and above) detector tuning varies by only 0.05% per millimolar, meaning that dramatic fluctuations of over 10 mM in ionic strength would be required to produce MRI changes comparable to those elicited by even the smallest detectable voltage or photonic inputs. Similarly, detector responses to temperature variation were minimal. Even across an unphysiologically large range of temperatures from ~22° C. to 37° C., the experimentally determined tuning characteristics as a function of input are barely affected (FIG. 12B). The MRI scanner's $B_0$ field is another environmental parameter that can vary somewhat, typically on the order of 10 parts per million[38], due primarily to spatial variations in magnetic susceptibility in tissue. To model such effects, the detector's response to tuning offsets by up to 1 MHz from the main $B_0$ resonance frequency were examined and it was shown that under all conditions the tuning behavior as a function of input remains approximately unchanged (FIG. 12C). Local $B_1$ fields produced by the scanner's main coil can also vary somewhat in realistic scanning conditions. Such inhomogeneities are not expected to affect the interpretability of detector-mediated responses, however, because the detector's signal enhancement simply scales with whatever the local $B_1$ is (see FIGS. 4A-4E, FIG. 7, and FIGS. 8A-8B). Differences in the angular orientation of a detector could affect inductive coupling to the main coil and thus alter the magnitude of signal enhancements, but even these would not affect the profile of relative detector responses to gate inputs of varying amplitude.

Example: Performance in Clinically-Relevant Settings

Initial assessment of the disclosed detectors was performed at a field strength of 9.4 T, but potential clinical applications would likely involve considerably lower $B_0$ fields. To test detector performance at a clinically relevant magnetic field strength, a detector having diameter d of 3 mm, tuned for operation in a 3 T MRI scanner was constructed and its performance with results obtained at 9.4 T was compared (FIGS. 13A-13C). The experimental dynamic range is similar at both field strengths, although the detector response reaches an asymptote at somewhat lower gate input voltage at lower field (400 mV vs. 500 mV). Modeled performance of detectors as a function of field strength (FIG. 13C) shows that the minimum detectable gate input signal also increases at lower field. At 3 T, a detector with diameter d=3 mm and $t_m$=10 µm is predicted to detect 14.6 mV or $2.9 \times 10^9$ p/s inputs, whereas a similar device tuned to operate at 9.4 T could detect somewhat weaker inputs of 6.4 mV or $1.3 \times 10^9$ p/s.

A limitation on the application of some implantable electronic devices in biomedical settings is the propensity of such devices to deposit energy into biological tissue, leading to local heating and potential damage. The amount of energy deposition depends on an interaction among multiple device- and tissue-dependent factors that together determine the specific absorption rate (SAR). A simple upper bound on the SAR for a detector can be calculated simply by determining the total power dissipated in the detector itself and normalizing this by the tissue volume likely to be affected by each individual device, here approximated as a sphere equal to twice the device diameter. To compute this quantity, the simulation approach was used to determine the peak instantaneous power deposition, assuming operation at 400 MHz with a typical main coil RF field strength ($B_1$=2 µT). It was found that upper bounds on SAR ranged from $8 \times 10^{-3}$ W/kg for a detector having diameter d of 1 mm to $3 \times 10^{-4}$ W/kg for a detector having diameter d of 5 mm (FIG. 14). Using a detector having diameter d of 3 mm operated continuously for two hours with a pulse sequence repetition time of 2 seconds in contact with a 1 mL buffer sample, it was found that mean temperature rose by at most ~1° C., indicating a combined power deposition from the main $B_1$ coil and the detector of less than $6 \times 10^{-4}$ W across the specimen. Such values fall well within safety margins of several W/kg specified by the US Food and Drug Administration, and indicate that the disclosed detectors will be safe for use in animals and people.

Example: Detection of Bioluminescence In Vitro and In Vivo

To examine performance of the disclosed detectors in biological settings, it was attempted to modulate detector-mediated MRI signals using biogenic sources. Bioluminescent detection (FIG. 6A) was chosen as the initial focus because this modality does not require electrical contact between the sensor and the specimen being measured. Using the photosensitive detector with diameter d=3 mm, the MRI signal was examined when the detector was stimulated by a 7.8 µM luciferase solution, following addition of 1 mM D-luciferin and 1 mM ATP. The enzymatic reaction generated sufficient light flux to detune the detector, producing an MRI signal decrease of 16±7%, with respect to the signal observed in the absence of luciferase (FIG. 6B). Minimal MRI signal changes of only 0.4±5.4% were measured in the presence of luciferase, but without luciferin or ATP. Using network analyzer measurements, it was verified that the luciferase-mediated response in FIG. 6B was caused by detuning of the detector; luciferase activity decreased the detector's Q value by 3.8±0.8% and induced a tuning frequency shift of 2.7 MHz (FIG. 6C).

These measurements demonstrate the ability of the detector design to transduce bioluminescence signals to an MRI detectable signal change. It was next sought to determine whether endogenously expressed luciferase inside cells could produce similar effects. HEK293 cells expressing an engineered luciferase (NanoLuc) were placed in proximity to the 3 mm diameter d detector. Upon addition of the luciferin analog furimazine, a 3.6±0.6% decrease in MRI signal that persisted for more than 60 minutes was observed (FIG. 15). No signal change was observed distally from the device.

Cellular expression of luciferase is widely used in vivo as a reporter for cell density and status in animal models of tumorigenesis and transplantation; it was therefore asked whether a detector could reveal the presence of luciferase-expressing cells in a living animal. NanoLuc-expressing HEK293 cells were xenografted into the cerebral cortex of anesthetized rats, and detectors having diameter d of 3 mm were implanted over the cells (FIGS. 6D-6E). MRI scanning was performed before, during, and after intracranial injection of 1 mM furimazine substrate (3 µL) proximal to the cell implantation sites. During injection and spreading of the furimazine in the brain parenchyma, a significant average signal decrease of up to 16.2±2.3% (t-test p=0.006, n=4) was observed, that developed and persisted for over 80 minutes (FIGS. 6F-6G), consistent with infiltration of furimazine into the NanoLuc-expressing cell implants and subsequent stimulation of the photosensitive detectors. This mean signal change was 4.5 times the amplitude produced by $10^4$ cells/µL in the in vitro experiment of FIG. 15, and therefore suggests that the MRI signal change observed in vivo arose from approximately $5 \times 10^4$ cells/µL in the sensitive area of the detector.

The MRI change produced by the detector in the vicinity of bioluminescent cells and furimazine injection was significantly different from variations of the MRI signal distal to the detectors (paired t-test p=0.02, n=4), demonstrating that the detectors themselves mediated the observed signal changes. Neither $T_1$- nor $T_2$-weighted MRI scans performed after the experiments showed any evidence of tissue disruption. Furthermore, when the experiments of FIGS. 6F-6G were repeated with control injections of a fluid lacking furimazine, a statistically insignificant mean MRI intensity increase of 0.4±1.3% was observed (t-test p=0.8, n=3; FIG.

16). In addition to verifying that the signals documented in FIGS. 6F-6G arise from bioluminescence detection by the detectors, the absence of MRI changes in the vehicle control time courses shows that detectors can perform stably, without clearly discernable signal drift or biotoxicity, for periods of over two hours in vivo.

In the experiments of FIGS. 6D-6G, detector responses to bioluminescent cells in rat brain are slow and monotonic, likely reflecting the combination of diffusive spreading of the furimazine substrate from its infusion site, and the relatively constant metabolism of furimazine by NanoLuc-expressing cells. Such time courses are qualitatively consistent with bioluminescence time courses previously observed in vivo, but do not indicate intrinsic temporal limitations of the detector itself. To assess the detector's ability to function on a much faster time scale, an implanted detector was stimulated directly with a fiber optic light source and monitored its response characteristics in vivo (FIGS. 17A-17C). Repeated cycles of light delivery and rest show that the detector rapidly cycles between tuned and detuned states with no apparent hysteresis on the time scale of the scan duration. The results also provided an additional testament to the stable performance of detectors in vivo, with no observable attenuation of the light-dependent responses over the 20 min acquisition time investigated. An average MRI signal decrease of 12.7±0.7% was observed, with a coefficient of variation of ~10% denoting reproducible performance over four stimulation blocks. These measurements therefore collectively demonstrate that the disclosed detectors can detect biologically relevant electromagnetic fields reversibly and over a range of time scales in living animals.

Example: Experimental Discussion

The results demonstrate a new principle for minimally invasive detection of biological signals using biosensitive implantable microdevices that produce localized image changes in MRI. The disclosed detectors accomplish this using simple resonant circuits that require no external power and are detuned by input to a FET. The disclosed detectors offer several advantages with respect to other implantable device technologies: they are unwired and interact only passively with detection hardware, they do not need to transmit signals out of the body, and they can readily be spatially multiplexed in scalable fashion, in conjunction with MRI-based localization. The detector design closely parallels that of detunable surface coils for MRI, but on a miniature scale and using components sensitive to biologically realistic inputs. Detectability of voltage signals as low as 5.3 mV and luminescent input as low as $1\times10^9$ p/s have been shown. A light sensitive detector was tested in vivo and successfully monitored the output of a luciferase gene reporter expressed in a tumor cell model. This was achieved in conjunction with standard MRI hardware, without danger of excessive local energy deposition.

The millimeter-scale devices used in this study could be deployed in many organs of the body where external monitoring of electromagnetic fields is desired. The detector used for the in vivo experiments in particular had a 3 mm diameter d, comparable to some electronic implant designs that function by different principles. A goal for future development, however, will be to further miniaturize the detectors in order to permit placement using endoscopic procedures, or perhaps even infusion into vasculature. The theoretical calculations provide a basis for such efforts, showing that ImpACTs with submillimeter diameters d are feasible using multiturn designs (FIG. 10). The $t_m$ values of several microns required for optimum functionality of such detectors can easily be achieved with electroplating techniques used for microfabricated tethered MRI diagnostics devices. Some studies have demonstrated high performance microscale coils using wire bonding, but this limits scalability due to the serial fabrication process involved. The presently disclosed design, by contrast, employs processes that are easy to implement in parallel, providing a route for mass production with low manufacturing costs.

Another goal for future development of the disclosed detectors is to expand the scope of potential applications in vivo. For chronic applications in animals or people, this will involve ensuring that the detectors are stable and biocompatible over long periods of time. Results presented already demonstrate consistent MRI signal in proximity to detectors over periods of several hours (FIG. 16), as well as reproducible, repeated responses to equivalent stimuli across multiple animals (FIGS. 6A-6G) and multiple cycles of stimulation (FIGS. 17A-17C). Further applications may benefit in addition from passivation strategies that promote tissue compatibility and effective performance of the devices over days, months, or years. Expanding the scope of utility may also involve exploring how the detectors could be used in conjunction with diverse magnetic resonance hardware. Although compatibility of the detectors has been shown with MRI-based detection in both conventional clinical and small-bore scanners, multiplexed detection of the disclosed detectors could be possible using much more portable systems, albeit with some loss of sensitivity at lower $B_0$ field (FIGS. 13A-13C).

When combined with any suitable detection hardware, the detectors validated here could be used in their current state to detect luminescent reporter gene expression in applications such as following tumor growth and treatment in animal models, studying lymphatic function mediated by engineered immune cells, or monitoring luciferase-expressing transplanted cells and tissues, potentially in human subjects. For each of these applications, the current light sensitivity of $\sim 1\times10^9$ p/s, should permit imaging of cellular events involving expression of $10^5$-$10^6$ copies of luciferase per cell, assuming enzyme turnover number ranging between 0.1 and 1 $s^{-1}$, with as few as $10^4$-$10^5$ cells in the vicinity of the 300×300 µm light sensitive area of the current detector. Integrating detectors with low dark current photodiodes would require additional components for more efficient RF power harvesting by the detector, but could permit detection of as little as $10^6$ p/s, enabling sensitivity to luminescent events involving more than an order of magnitude fewer cells or luciferin turnover events. These might for instance enable dynamic activity monitoring of calcium-sensitive bioluminescent probes such as aequorin, estimated to generate fluxes of $1.3\times10^3$ p/s per neuron when expressed in vertebrate brains.

The voltage-dependent device 500 characterized in FIGS. 5A-5E displays sensitivity to inputs of 5 mV or more in MRI experiments in vitro, and could also be applied for wireless measurements in more or less its present form. The device's 500 sensitivity is sufficient in principle for dynamic detection of long-range extracellular potentials arising from activated cell populations in neural and muscle tissue. If the device is placed in close apposition to single cells, even individual action potentials could be detectable. Detection of millisecond-timescale transient electrophysiological events is possible provided that those events produce input to the device 500 during application of the MRI pulse. As such, the short duration of intracellular and extracellular potentials in electrically active tissue does not present a challenge to their detection using the disclosed detectors. Improved sensitivity for detection of single cell electrical potentials could be achieved by optimizing FET I-V characteristics for more robust detuning of the detectors, potentially using nanowire-based FETs that have been applied in the past for wired electrophysiology measurements.

Another exciting avenue for further development will be the sensitization of detectors to chemical signals, which can be performed via functionalization of the gate electrode of ion-sensitive FETs with biochemically active agents such as enzymes and antibodies. This would enable detection of diverse analytes with high specificity, in proportion to their concentration, via enzymatic or biochemical recognition events that alter transconductance of the FET. Along with further applications to detection of electromagnetic fields, the possibility of chemical detection using the disclosed detectors highlights the versatility of this family of detectors for dynamic forms of functional imaging that leverage the spatiotemporal resolution and whole-body volumetric readout capabilities of MRI.

Example: Simulations

Performance of the disclosed detector was simulated using equivalent circuit models implemented in PSpice (Cadence Design Systems, Chelmsford, Mass.). The MRI scanner's transmit-receive coil was represented by a resistor-inductor-capacitor (RLC) circuit, assuming a 78 mm diameter d (L=143.3 nH), 50 Ohm impedance and a sinusoidal voltage source as coil output. The main coil was inductively coupled to the detector (coupling coefficient k=0.00275-0.275), which was represented by another RLC circuit, having connected in parallel a FET component. The detector inductance ranged from 0.2 to 32 nH, and the capacitance ranged from 4.8 to 791.7 pF. The resistance was calculated based on sheet resistance considerations and skin depth at 400 MHz. Sensitivity profiles of the modeled FET devices simulated here were obtained with reference to published characteristics of 2N5486 MOSFET from Central Semiconductor Corp. (Hauppauge, N.Y.) and the SFH3310 photoFET from Osram Opto Semiconductors (Regensburg, Germany), respectively.

Current output from the model was converted to magnetic field near the detector ($B_{detector}$) by using the Biot-Savart law for magnetic field produced by a current loop, and the ratio between $B_{detector}$ and the $B_1$ of the main coil was used as an estimate of MRI signal amplification due to the device. Justification for this approach is that for a wide family of MRI pulse protocols, including the gradient echo methods used in this paper, the MRI signal amplitude detected is proportional to sin(a), where a is the flip angle of the excitation pulse. Since a is in turn directly proportional to the local RF field during the excitation pulse, the local amplification of this field (as reflected by $B_{detector}/B_1$) will also determine the local amplification of MRI signal. This analysis applies to low flip angles, significantly less than 90°, as typically used in $T_1$-weighted imaging. For larger flip angles, the relationship between local $B_1$ enhancement and resulting MRI signal will be more complex, but may nevertheless be analytically derived. Note that this analysis ignores the potential effect of detector detuning on signal reception during the acquisition phase of the MRI pulse sequence; this effect is harder to model, but if present, would synergize with effects due to detector tuning during pulse generation.

Example: Calculation of Power Dissipation

An upper bound on the maximum local specific absorbance rate (SAR) of a detector was estimated by calculating the maximum instantaneous power (P) deposited in the detector during an RF pulse and normalizing this by a spherical volume of tissue (V) around the detector with twice the diameter d of the detector. This volume was chosen conservatively to reflect the maximal density at which multiple functional detectors could be spaced in tissue, with a separation of twice their diameter minimizing the potential for electromagnetic coupling between the devices. In most applications, the inter-detector spacing and corresponding volumes of power dissipation are likely to be much greater. Under the simulation conditions, the calculation is as follows:

$$\frac{P}{V} = \frac{\rho I_{detector}^2 R_{detector}}{4/3 \pi d^3} \quad (1)$$

where $\rho$ is the tissue density (approximately 1 kg/L), $R_{detector}$ is the detector impedance at 400 MHz, and $I_{detector}$ is the current induced in the detector, computed using the $B_{detector}/B_1$ ratios of FIG. 4C and assuming an applied RF field of 2 µT. The value of 2 µT for the scanner's RF pulse amplitude is chosen by assuming a pulse width ($t_p$) of 1 ms and a flip angle ($\alpha$) of 30°, using the formula:

$$B_1 = \frac{\alpha}{\gamma t_p} \quad (2)$$

with proton gyromagnetic ratio γ of 42.6 MHz/T. The P/V values computed using Eq. 1 and presented in FIGS. 11A-11B are likely to be substantial overestimates of the actual SAR, for three reasons: (1) because of the sparse duty cycle of pulsing in a typical MRI experiment (usually less than 1%); (2) because only a fraction of the power dissipated in the detector is actually likely to be transferred into the tissue as heat; and (3) as noted above, because the tissue volume over which power can be spread will likely be significantly greater than twice the detector diameter d.

Example: Device Fabrication and Characterization

Circuits were fabricated using standard printed-circuit single turn inductors with 10 µm gold-plated copper as conductive layer. Coil radius ranged from 500 µm to 5 mm with line width of 0.1-1 mm. Coils were soldered to trimmer capacitors with adjustable capacitance of 5.5-30 pF (Knowles Voltronics #JR300, Cazenovia, N.Y.). For voltage measurements, N-Channel 400 MHz RF MOSFETs with internal capacitance of 5 pF (Central Semiconductor Corp. #2N5486) were used. For MRI photodetection and bioluminescence measurements NPN phototransistors with 570 nm wavelength peak sensitivity and collector emitter capacitance of 2.2-4.0 pF (Osram Opto Semiconductors #SFH3310) were used. The photon-sensitive area of these components was 300×300 µm. For bioluminescence measurements outside of the MRI scanner, the IVIS Spectrum In Vivo Imaging System (PerkinElmer #124262, Waltham, Mass.) was used. Current measurements were made using a custom-made amperometer circuit and 10 GHz oscilloscope (Keysight Technologies #DSO81004B, Santa Rose, Calif.). Resonance frequency characterization was performed using RF network analyzer (Keysight Technologies, #E5061A) by way of reflected amplitude measurements using a loop antenna comprised of 2 mm copper-shielded coaxial silver wire (Pasternack #RG402-U, Irvine, Calif.), placed 0.5 mm above the detector's inductor. For water phantom measurements, 0.5 mL microcentrifuge tubes were cut and cured on top of the detector coils using epoxy glue. Temperature measurements were performed using SurgiVET Advisor monitor and V3417 temperature probe (Smiths Medical, Norwell, Mass.).

Example: Magnetic Resonance Imaging Validation and Data Analysis

Magnetic resonance imaging was performed primarily using a 9.4 T Avance II MRI scanner (Bruker Instruments, Ettlingen, Germany). Additional measurements at clinical field were performed using a Siemens (Erlangen, Germany) 3 T MAGNETOM Tim Trio scanner. Detectors were cured to polymer tubes for measurement in solution, and placed within a birdcage transmit-receive imaging volume coil (inner diameter 78 mm). Response to light intensity was done in light tight chambers. Both $T_1$- and $T_2$-weighted scans with 0.1-1 mm slice thickness across the surface of the detectors were acquired using gradient echo and fast spin echo pulse sequences. Echo time (TE) of 15.6 ms and repetition times (TR) of 250 and 787 ms were used. Data matrices of 64×64, 128×128, and 256×256 points were taken, with 1-10 averages, and total scan time ranging between 16 seconds and 10 minutes. Intensity values in square regions of interest at the center of the detector surface were determined from reconstructed magnitude images and compared with baseline values from regions distal to the detector. Analysis was performed using custom routines written in MATLAB. Time lapse scans for functional imaging were obtained using a gradient echo pulse sequence with a flip angle of 30°, TR of 236 ms, TE of 15.6 ms, field of view (FOV) of 25.6×25.6 mm, data matrix of 128×128 points, and 1 mm coronal slice thickness, with 16 second scan time. Scans were obtained consecutively for 60 minutes. Post-processing of MRI data was performed using customized routines in MATLAB (Mathworks, Natick, Mass.). Raw images were analyzed per region of interest around inductor element of the detector for the quantification of signal amplitude before and after detuning.

Example: Cellular Expression of Luciferase

Phantom measurements were taken using either dionized water or phosphate buffer saline, at pH 7.4, at room temperature. Magnetic resonance imaging of biological luminescence was performed in phosphate buffered saline, using recombinant luciferase from Photinus pyralis (Sigma Aldrich, #SRE0045, Natick, Mass.) at a concentration of 7.8 µM and initial volume of 100 µL. D-luciferin (Sigma Aldrich, #L9504), at concentration of 7.8 mM in argon-bubbled dionized water and equimolar concentration of sodium bicarbonate, and adenosine 5'-triphosphate (ATP) disodium salt hydrate (Sigma Aldrich, Cat #A2383) at a concentration of 7.8 mM, were each dissolved at a volume of 50 µL and were both mixed with luciferase solution during MRI to achieve working concentration of 3.9 µM of luciferase, and 3.9 mM of luciferin and ATP. For bioluminescence cell measurements a HEK293 cell line transfected with NanoLuc engineered luciferase plasmid (Promega #N1441, Madison, Wis.) was used. Bioluminescence was measured 48 hours after transfection by adding 1-5 mM furimazine (Promega, #N205A) to 10 million cells per mL in Tris buffer at the phototransistor component of device.

Example: Animal Use

Male Sprague-Dawley rats (250-300 g) were purchased from Charles River Laboratories (Wilmington, Mass.) and used for all in vivo experiments. Animals were housed and maintained on a 12 hr light/dark cycle and permitted ad libitum access to food and water. All procedures were performed in strict compliance with US Federal guidelines, with oversight by the MIT Committee on Animal Care.

Example: MRI Detection of Luciferase-Expressing Cells In Vivo

Intracerebral guide cannula were implanted surgically to facilitate intracranial injection of furimazine in MRI experiments, emulating previously described methods[57]. Animals were anesthetized with isoflurane (4% induction, 2% maintenance), shaved, and mounted on a rodent stereotaxic device (Kopf Instruments, Tujunga, Calif.) with heating pad. Heart rate and blood oxygenation were continuously monitored using a pulse oximeter (Nonin Medical, Plymouth, Minn.) during all subsequent procedures. The scalp was retracted and two small holes were drilled into the skull, 7 mm and 9 mm posterior to bregma and 0.5 lateral to the midline. An MRI-compatible 2 mm-long guide cannula (22 gauge; PlasticsOne, Roanoke, Va.) was implanted at the anterior site. 10 µL of NanoLuc-expressing HEK293 cell slurry (containing ~5 million cells) was injected into the cortex at the posterior site, and a detector was implanted over the cells. A custom fabricated plastic headpost was attached to the skull in front of the guide cannula, and dental cement was applied to secure all implants rigidly in place. Buprenorphin (0.05 mg/kg) was injected subcutaneously during surgery. An MRI-compatible injection cannula (3 mm long below pedestal, PlasticsOne) was connected to microtubing pre-filled with 5 µL 7.8 µM furimazine. The injection cannula was slowly lowered into the previously implanted guide cannula while infusing furimazine at a small injection rate to prevent air from becoming trapped during insertion. The injection cannula was then secured to the guide cannula with dental cement, and the injection was paused.

Each animal was then transferred to a plexiglass cradle covered with a water heating blanket to maintain body temperature, and inserted into a transmit-receive volume coil (Bruker Instruments, Billerica, Mass.). The animal was positioned at the isocenter of a 9.4 T Bruker Avance II scanner (Bruker Instruments). Heart rate and oxygen saturation levels were monitored throughout the scan using Nonin 8600V pulse oximeter (Nonin Medical, Plymouth, Minn.), and breathing and expired $CO_2$ were monitored using a SurgiVet V9004 Capnograph (Waukesha, Wis.). Heart rate was maintained at 360-380 bpm. Animals were maintained with continuous delivery of 1.5% isoflurane for the duration of the scanning sessions.

For in vivo MRI analysis, $T_1$-weighted scan series and $T_2$-weighted anatomical scans were obtained from each animal. Multislice anatomical images with 200 µm in-plane resolution over six 1 mm sagittal slices were obtained using a rapid acquisition with relaxation enhancement (RARE) pulse sequence with a TR of 2 sec, TE of 14 ms, RARE factor of 8, field of view of 25.6×25.6 mm, data matrix of 128×128 points, 4 averages and a total scan time of 80 sec. Scan series for functional imaging were obtained using a gradient echo pulse sequence with a flip angle of 30°, TR of 126 ms, TE of 10 ms, FOV of 25.6×25.6 mm, data matrix of 128×128 points, and 1 mm sagittal slice thickness, with 16 s scan time per image. Scans were obtained consecutively for 120 minutes; from t=5 to 35 minutes, furimazine was infused at a constant rate of 0.1 µL/min.

Example: Additional Design Considerations

To evaluate the detector circuit metal layer thickness ($t_m$) required for sensing electrical or photonic input, the response of detectors was simulated with feasible $t_m$ values ranging between 500 nm and 10 µm. Throughout most of this range, reducing thickness $t_m$ increases the impedance of its inductor component, lowering the device's Q and reducing the coupling efficiency between the detector and the MRI coil. FIGS. 8A-8B show that this has the effect of reducing the change in $B_{detector}/B_1$ that can be achieved by modulating inputs to the detector, lowering its sensitivity. For detectors with thickness $t_m$ greater than 8 µm (thicker than twice the skin depth at 400 MHz), performance is approximately constant, with inputs producing up to 63% changes in $B_{detector}/B_1$. For $t_m<1$ µm, no discernable change in $B_{detector}/B_1$ can be produced however. Although the simulated data of FIGS. 4A-4E and FIGS. 8A-8B establish lower bounds of diameter d=1 mm and thickness $t_m$=1 µm on the fabrication of sensitive detectors produced with single turn inductors and commercially available compact FETs, additional design factors were examined that could permit improved sensitivity or further miniaturization of the detectors in future work. FIGS. 9A-9B show that one route to achieving improved sensitivity is to increase the FET or photoFET's transconductance ($g_m$), defined as the reciprocal of its drain-source resistance in the fully open state. By increasing transconductance $g_m$ four-fold from the value of $5\times10^{-3}$ used in the simulations of FIGS. 4A-4E, the predicted response of a 1 mm diameter d ImpACT to a 10 mV input increases by 79%, and the minimum detectable input reaches 11.3 mV or $2.3\times10^9$ p/s. A second strategy for improving sensitivity involves increasing the number of turns of the detector inductor coil. FIG. 10 shows that devices with diameters d of 1 mm, 500 µm, 250 µm, and 100 µm, can achieve 1% changes in $B_{detector}/B_1$ in response to inputs of 5.6 mV, 5.8 mV, 9.9 mV, and 33 mV respectively.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the embodiments described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "user." It should be appreciated that a "user" need not be a single individual, and that in some embodiments, actions attributable to a "user" may be performed by a team of individuals and/or an individual in combination with computer-assisted tools or other mechanisms.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A detector comprising:
   an antenna;
   an RLC circuit including an inductor, a capacitor, and a resistor, wherein the RLC circuit is electrically coupled to the antenna;
   a transistor configured to change a resonant frequency of the RLC circuit when a predetermined physical parameter is detected by the transistor; and
   a substrate supporting the antenna, the RLC circuit, and the transistor, wherein the detector has a maximum dimension that is less than or equal to 1 centimeter (cm), and wherein the detector is configured to be injected and/or implanted within a subject.

2. The detector of claim 1, wherein the transistor is connected in series with the capacitor.

3. The detector of claim 1, wherein the transistor is connected in parallel with one of the inductor, capacitor, or resistor.

4. The detector of claim 1, wherein the inductor, capacitor, and resistor are connected in series.

5. The detector of claim 1, wherein the antenna is the inductor.

6. The detector of claim 1, wherein the transistor is selected from the group consisting of a: Ion sensitive FET (ISFET), photo-sensitive FET (PHOTOFET), Chemically sensitive FET (CHEMFET), Biologically sensitive FET (BioFET), Enzyme Modified FET (EnFET), antibody sensitive and antigen functionalized FET (ImmunoFET), nanowire FET (NWFET), silicon nanowire FET (silicon NWFETs), Bipolar junction transistors (BJTs) in NPN or PNP configuration, and Magnetic Field Sensitive metal oxide silicon FET (MAGFET), or a combination of the forgoing.

7. The detector of claim 1, wherein the predetermined physical parameter is a concentration of a biochemical analyte.

8. The detector of claim 1, wherein the predetermined physical parameter is an electrical signal.

9. The detector of claim 1, wherein the predetermined physical parameter is an optical signal.

10. The detector of claim 1, wherein the antenna couples with the main coil of a magnetic resonance imaging system.

11. The detector of claim 10, wherein detection of the predetermined physical parameter changes a gate-source voltage across the transistor and the resonant frequency of the RLC circuit.

12. The detector of claim 1, wherein the detector is configured to be free-standing when injected and/or implanted within the subject.

13. A device, comprising:
    a substrate; and
    a circuit supported by the substrate and configured to electromagnetically couple to an imaging device based on resonant characteristics of the circuit, wherein the circuit is further configured to alter the resonant characteristics in response to detecting a physiological and/or biochemical parameter, wherein the device is configured to be injected and/or implanted within a subject, and wherein the device has a maximum dimension that is less than or equal to 1 centimeter (cm).

14. The device of claim 13, wherein in response to detecting the physiological and/or biochemical parameter, the circuit is configured to alter at least one selected from the group of:
    a resonant frequency of the circuit; and
    an amount of resonance damping at the resonant frequency.

15. The device of claim 13, wherein the resonant characteristics depend on a resistance, capacitance, and inductance of the circuit, and wherein the circuit includes a transistor configured to alter the resistance, capacitance, and/or inductance of the circuit in response to detecting the physiological and/or biochemical parameter.

16. The device of claim 15, wherein the transistor is selected from the group consisting of a: Ion sensitive FET (ISFET), photo-sensitive FET (PHOTOFET), Chemically sensitive FET (CHEMFET), Biologically sensitive FET (BioFET), Enzyme Modified FET (EnFET), antibody sensitive and antigen functionalized FET (ImmunoFET), nanowire FET (NWFET), silicon nanowire FET (silicon NWFETs), Bipolar junction transistors (BJTs) in NPN or PNP configuration, and Magnetic Field Sensitive metal oxide silicon FET (MAGFET), or a combination of the forgoing.

17. The device of claim 13, wherein the circuit is further configured to operate using power received through electromagnetically coupling to the imaging device.

18. The device of claim 13, wherein the imaging device is a magnetic resonance imaging (MRI) system.

19. The device of claim 13, wherein the circuit is configured to detect the physiological and/or biochemical parameter in the form of:
    a voltage; and/or
    an optical signal.

20. The device of claim 13, wherein the device is configured to be injected and/or implanted within a subject for at least one day.

* * * * *